US009642616B2

United States Patent
Nobles et al.

(10) Patent No.: US 9,642,616 B2
(45) Date of Patent: May 9, 2017

(54) METHOD AND APPARATUS FOR APPLYING A KNOT TO A SUTURE

(71) Applicant: Nobles Medical Technologies, Inc., Fountain Valley, CA (US)

(72) Inventors: Anthony A. Nobles, Fountain Valley, CA (US); Steven E. Decker, Anaheim, CA (US); Egbert Ratering, Amsterdam (NL)

(73) Assignee: Nobles Medical Technologies, Inc., Fountain Valley, CA (US)

( * ) Notice: Subject to any disclaimer, the term of this patent is extended or adjusted under 35 U.S.C. 154(b) by 756 days.

(21) Appl. No.: 13/905,225

(22) Filed: May 30, 2013

(65) Prior Publication Data

US 2013/0261645 A1    Oct. 3, 2013

Related U.S. Application Data

(60) Continuation of application No. 13/489,573, filed on Jun. 6, 2012, now Pat. No. 8,469,975, which is a (Continued)

(51) Int. Cl.
*A61B 17/04* (2006.01)

(52) U.S. Cl.
CPC ...... *A61B 17/0491* (2013.01); *A61B 17/0485* (2013.01); *A61B 17/0487* (2013.01);
(Continued)

(58) Field of Classification Search
CPC ............ A61B 17/0485; A61B 17/0491; A61B 17/0487; A61B 17/0467; A61B 17/0469;
(Continued)

(56) References Cited

U.S. PATENT DOCUMENTS

| 118,683 A | 9/1871 | Bruce |
|---|---|---|
| 1,064,307 A | 6/1913 | Fleming |

(Continued)

FOREIGN PATENT DOCUMENTS

| AU | 2006251579 | 11/2006 |
|---|---|---|
| CN | 101495049 | 12/2010 |

(Continued)

OTHER PUBLICATIONS

Invitation to Pay Additional Fees, mailed Dec. 6, 2006 in corresponding International Application No. PCT/US2006/023676, 6 pages.

(Continued)

*Primary Examiner* — Todd J Scherbel
*Assistant Examiner* — Son Dang
(74) *Attorney, Agent, or Firm* — Knobbe, Martens, Olson & Bear, LLP

(57) ABSTRACT

A knot placement device allows a physician to apply a knot for securing two or more suture ends extending from an incision in a vessel or organ of a patient relative to each other in order to seal an opening in the vessel or organ. The knot placement device has a handle and an elongate shaft and a push rod slidably inserted in said shaft. A knot is disposed in the distal end of the shaft. An actuator on the handle may be depressed to distally advance said push rod relative to said shaft and thereby distally advance said knot. The knot may include a knot body having an inner cavity and a plug sized to fit securely within the inner cavity. In use, the plug may be inserted into the inner cavity of the knot body to fixedly hold two or more suture ends between the knot body and the plug.

11 Claims, 20 Drawing Sheets

Related U.S. Application Data division of application No. 11/455,894, filed on Jun. 19, 2006, now Pat. No. 8,197,497.

(60) Provisional application No. 60/693,582, filed on Jun. 20, 2005, provisional application No. 60/709,485, filed on Aug. 19, 2005.

(52) U.S. Cl.
CPC ....... *A61B 17/0467* (2013.01); *A61B 17/0469* (2013.01); *A61B 2017/045* (2013.01); *A61B 2017/0459* (2013.01); *A61B 2017/0488* (2013.01)

(58) Field of Classification Search
CPC ...... A61B 2017/045; A61B 2017/0459; A61B 2017/0488
See application file for complete search history.

(56) References Cited

U.S. PATENT DOCUMENTS

| | | |
|---|---|---|
| 1,989,919 A | 2/1935 | Everitt |
| 2,473,742 A | 6/1949 | Auzin |
| 2,548,602 A | 4/1951 | Greenburg |
| 2,637,290 A | 5/1953 | Sigoda |
| 2,738,790 A | 3/1956 | Todt, Sr. et al. |
| 2,849,002 A | 8/1958 | Oddo |
| 2,945,460 A | 7/1960 | Kagiyama |
| 3,241,554 A | 3/1966 | Coanda |
| 3,292,627 A | 12/1966 | Harautuneian |
| 3,394,705 A | 7/1968 | Abramson |
| 3,664,345 A | 5/1972 | Dabbs et al. |
| 3,665,926 A | 5/1972 | Flores |
| 3,774,596 A | 11/1973 | Cook |
| 3,828,790 A | 8/1974 | Curtiss et al. |
| 3,831,587 A | 8/1974 | Boyd |
| 3,842,840 A | 10/1974 | Schweizer |
| 3,877,434 A | 4/1975 | Ferguson et al. |
| 3,882,852 A | 5/1975 | Sinnreich |
| 3,882,855 A | 5/1975 | Schulte et al. |
| 3,888,117 A | 6/1975 | Lewis |
| 3,903,893 A | 9/1975 | Scheer |
| 3,946,740 A | 3/1976 | Bassett |
| 3,946,741 A | 3/1976 | Adair |
| 3,952,742 A | 4/1976 | Taylor |
| 3,976,079 A | 8/1976 | Samuels |
| 4,052,980 A | 10/1977 | Grams et al. |
| RE29,703 E | 7/1978 | Fatt |
| 4,107,953 A | 8/1978 | Casillo |
| 4,119,100 A | 10/1978 | Rickett |
| 4,164,225 A | 8/1979 | Johnson et al. |
| 4,230,119 A | 10/1980 | Blum |
| 4,291,698 A | 9/1981 | Fuchs et al. |
| 4,299,237 A | 11/1981 | Foti |
| 4,307,722 A | 12/1981 | Evans |
| 4,351,342 A | 9/1982 | Wiita et al. |
| 4,417,532 A | 11/1983 | Yasukata |
| 4,423,725 A | 1/1984 | Baran et al. |
| 4,447,227 A | 5/1984 | Kotsanis |
| 4,457,300 A | 7/1984 | Budde |
| 4,484,580 A | 11/1984 | Nomoto et al. |
| 4,512,338 A | 4/1985 | Balko et al. |
| 4,546,759 A | 10/1985 | Solar |
| 4,553,543 A | 11/1985 | Amarasinghe |
| 4,573,966 A | 3/1986 | Weikl et al. |
| 4,589,868 A | 5/1986 | Dretler |
| 4,610,662 A | 9/1986 | Weikl et al. |
| 4,617,738 A | 10/1986 | Kopacz |
| 4,662,068 A | 5/1987 | Polonsky |
| 4,664,114 A | 5/1987 | Ghodsian |
| 4,734,094 A | 3/1988 | Jacob et al. |
| 4,744,364 A | 5/1988 | Kensey |
| 4,750,492 A | 6/1988 | Jacobs |
| 4,771,776 A | 9/1988 | Powell et al. |
| 4,774,091 A | 9/1988 | Yamahira et al. |
| 4,794,928 A | 1/1989 | Kletschka |
| 4,795,427 A | 1/1989 | Helzel |
| 4,796,629 A | 1/1989 | Grayzel |
| 4,824,436 A | 4/1989 | Wolinsky |
| 4,827,931 A | 5/1989 | Longmore |
| 4,841,888 A | 6/1989 | Mills et al. |
| 4,861,330 A | 8/1989 | Voss |
| 4,898,168 A | 2/1990 | Yule |
| 4,923,461 A | 5/1990 | Caspari et al. |
| 4,926,860 A | 5/1990 | Stice et al. |
| 4,932,956 A | 6/1990 | Reddy et al. |
| 4,935,027 A | 6/1990 | Yoon |
| 4,954,126 A | 9/1990 | Wallsten |
| 4,957,498 A | 9/1990 | Caspari et al. |
| 4,972,845 A | 11/1990 | Iversen et al. |
| 4,981,149 A | 1/1991 | Yoon et al. |
| 4,983,116 A | 1/1991 | Koga |
| 4,984,564 A | 1/1991 | Yuen |
| 4,994,070 A | 2/1991 | Waters |
| 5,002,531 A | 3/1991 | Bonzel |
| 5,021,059 A | 6/1991 | Kensey et al. |
| 5,037,433 A | 8/1991 | Wilk et al. |
| 5,057,114 A | 10/1991 | Wittich et al. |
| 5,059,201 A | 10/1991 | Asnis |
| 5,065,772 A | 11/1991 | Cox, Jr. |
| 5,074,871 A | 12/1991 | Groshong |
| 5,078,743 A | 1/1992 | Mikalov et al. |
| 5,090,958 A | 2/1992 | Sahota |
| 5,100,418 A | 3/1992 | Yoon et al. |
| 5,104,394 A | 4/1992 | Knoepfler |
| 5,106,363 A | 4/1992 | Nobuyoshi |
| 5,108,416 A | 4/1992 | Ryan et al. |
| 5,108,419 A | 4/1992 | Reger et al. |
| 5,116,305 A | 5/1992 | Milder et al. |
| 5,122,122 A | 6/1992 | Allgood |
| 5,129,883 A | 7/1992 | Black |
| 5,133,724 A | 7/1992 | Wilson et al. |
| 5,135,484 A | 8/1992 | Wright |
| 5,160,339 A | 11/1992 | Chen et al. |
| 5,163,906 A | 11/1992 | Ahmadi |
| 5,167,223 A | 12/1992 | Koros et al. |
| 5,171,251 A | 12/1992 | Bregen et al. |
| 5,176,691 A | 1/1993 | Pierce |
| 5,192,301 A | 3/1993 | Kamiya et al. |
| 5,222,508 A | 6/1993 | Contarini |
| 5,222,941 A | 6/1993 | Don Michael |
| 5,222,974 A | 6/1993 | Kensey et al. |
| 5,224,948 A | 7/1993 | Abe et al. |
| 5,242,459 A | 9/1993 | Buelna |
| 5,281,234 A | 1/1994 | Wilk et al. |
| 5,281,237 A | 1/1994 | Gimpelson |
| 5,282,827 A | 2/1994 | Kensey et al. |
| 5,286,259 A | 2/1994 | Ganguly et al. |
| 5,290,249 A | 3/1994 | Foster et al. |
| 5,300,106 A | 4/1994 | Dahl et al. |
| 5,304,184 A | 4/1994 | Hathaway et al. |
| 5,308,323 A | 5/1994 | Sogawa et al. |
| 5,312,344 A | 5/1994 | Grinfeld et al. |
| 5,314,409 A | 5/1994 | Sarosiek et al. |
| 5,320,604 A | 6/1994 | Walker et al. |
| 5,320,632 A | 6/1994 | Heidmueller |
| 5,330,446 A | 7/1994 | Weldon et al. |
| 5,330,497 A | 7/1994 | Freitas et al. |
| 5,331,975 A | 7/1994 | Bonutti |
| 5,336,229 A | 8/1994 | Noda |
| 5,336,231 A | 8/1994 | Adair |
| 5,337,736 A | 8/1994 | Reddy |
| 5,339,801 A | 8/1994 | Poloyko |
| 5,342,306 A | 8/1994 | Don Michael |
| 5,342,385 A | 8/1994 | Norelli et al. |
| 5,342,393 A | 8/1994 | Stack |
| 5,350,399 A | 9/1994 | Erlebacher et al. |
| 5,356,382 A | 10/1994 | Picha et al. |
| 5,364,407 A | 11/1994 | Poll |
| 5,364,408 A | 11/1994 | Gordon |
| 5,368,601 A | 11/1994 | Sauer et al. |
| 5,370,618 A | 12/1994 | Leonhardt |
| 5,370,685 A | 12/1994 | Stevens |

(56) References Cited

U.S. PATENT DOCUMENTS

| | | |
|---|---|---|
| 5,374,275 A | 12/1994 | Bradley et al. |
| 5,380,284 A | 1/1995 | Don Michael |
| 5,382,261 A | 1/1995 | Palmaz |
| 5,383,854 A | 1/1995 | Safar et al. |
| 5,383,896 A | 1/1995 | Gershony et al. |
| 5,383,897 A | 1/1995 | Wholey |
| 5,383,905 A | 1/1995 | Golds et al. |
| 5,389,103 A | 2/1995 | Melzer et al. |
| 5,391,147 A | 2/1995 | Imran et al. |
| 5,391,174 A | 2/1995 | Weston |
| 5,395,383 A | 3/1995 | Adams et al. |
| 5,397,325 A | 3/1995 | Badia et al. |
| 5,403,329 A | 4/1995 | Hinchcliffe |
| 5,403,331 A | 4/1995 | Chesterfield et al. |
| 5,403,341 A | 4/1995 | Solar |
| 5,405,322 A | 4/1995 | Lennox et al. |
| 5,405,354 A | 4/1995 | Sarrett |
| 5,417,699 A | 5/1995 | Klein et al. |
| 5,417,700 A | 5/1995 | Egan |
| 5,423,777 A | 6/1995 | Tajiri et al. |
| 5,423,837 A | 6/1995 | Mericle et al. |
| 5,425,708 A | 6/1995 | Nasu |
| 5,425,737 A | 6/1995 | Burbank et al. |
| 5,425,744 A | 6/1995 | Fagan et al. |
| 5,429,118 A | 7/1995 | Cole et al. |
| 5,431,666 A | 7/1995 | Sauer et al. |
| 5,439,470 A | 8/1995 | Li |
| 5,445,167 A | 8/1995 | Yoon et al. |
| 5,447,515 A | 9/1995 | Robicsek |
| 5,452,513 A | 9/1995 | Zinnbauer et al. |
| 5,454,823 A | 10/1995 | Richardson et al. |
| 5,458,574 A | 10/1995 | Machold et al. |
| 5,458,609 A | 10/1995 | Gordon et al. |
| 5,462,560 A | 10/1995 | Stevens |
| 5,462,561 A | 10/1995 | Voda |
| 5,470,338 A | 11/1995 | Whitfield et al. |
| 5,474,572 A | 12/1995 | Hayhurst |
| 5,476,469 A | 12/1995 | Hathaway et al. |
| 5,476,470 A | 12/1995 | Fitzgibbons, Jr. |
| 5,496,332 A | 3/1996 | Sierra et al. |
| 5,499,991 A | 3/1996 | Garman et al. |
| 5,501,691 A | 3/1996 | Goldrath |
| 5,507,754 A | 4/1996 | Green et al. |
| 5,507,755 A | 4/1996 | Gresl et al. |
| 5,514,159 A | 5/1996 | Matula et al. |
| 5,520,609 A | 5/1996 | Moll et al. |
| 5,520,702 A | 5/1996 | Sauer et al. |
| 5,522,961 A | 6/1996 | Leonhardt |
| 5,527,321 A | 6/1996 | Hinchliffe |
| 5,527,322 A | 6/1996 | Klein et al. |
| 5,527,338 A | 6/1996 | Purdy |
| 5,540,658 A | 7/1996 | Evans et al. |
| 5,540,704 A | 7/1996 | Gordon et al. |
| 5,545,170 A | 8/1996 | Hart |
| 5,549,633 A | 8/1996 | Evans et al. |
| 5,558,642 A | 9/1996 | Schweich et al. |
| 5,558,644 A | 9/1996 | Boyd et al. |
| RE35,352 E | 10/1996 | Peters |
| 5,562,686 A | 10/1996 | Sauer et al. |
| 5,562,688 A | 10/1996 | Riza |
| 5,565,122 A | 10/1996 | Zinnbauer et al. |
| 5,571,090 A | 11/1996 | Sherts |
| 5,573,540 A | 11/1996 | Yoon |
| 5,584,835 A | 12/1996 | Greenfield |
| 5,584,861 A | 12/1996 | Swain et al. |
| 5,591,195 A | 1/1997 | Taheri et al. |
| 5,593,422 A | 1/1997 | Muijs Van de Moer et al. |
| 5,599,307 A | 2/1997 | Bacher et al. |
| 5,603,718 A | 2/1997 | Xu |
| 5,613,974 A | 3/1997 | Andreas et al. |
| 5,613,975 A | 3/1997 | Christy |
| 5,626,590 A | 5/1997 | Wilk |
| 5,630,833 A | 5/1997 | Katsaros et al. |
| 5,632,751 A | 5/1997 | Piraka |
| 5,632,752 A | 5/1997 | Buelna |
| 5,634,936 A | 6/1997 | Linden et al. |
| 5,637,097 A | 6/1997 | Yoon |
| 5,643,289 A | 7/1997 | Sauer et al. |
| 5,645,553 A | 7/1997 | Kolesa et al. |
| 5,662,663 A | 9/1997 | Shallman |
| 5,669,917 A | 9/1997 | Sauer et al. |
| 5,669,971 A | 9/1997 | Bok et al. |
| 5,674,198 A | 10/1997 | Leone |
| 5,681,296 A | 10/1997 | Ishida |
| 5,681,351 A | 10/1997 | Jamiolkowski et al. |
| 5,688,245 A | 11/1997 | Runge |
| 5,690,674 A | 11/1997 | Diaz |
| 5,695,468 A | 12/1997 | Lafontaine et al. |
| 5,695,504 A | 12/1997 | Gifford, III et al. |
| 5,697,905 A | 12/1997 | D'Ambrosio |
| 5,700,273 A | 12/1997 | Buelna et al. |
| 5,700,277 A | 12/1997 | Nash et al. |
| 5,707,379 A | 1/1998 | Fleenor et al. |
| 5,709,693 A | 1/1998 | Taylor |
| 5,716,329 A | 2/1998 | Dieter |
| 5,720,757 A | 2/1998 | Hathaway et al. |
| 5,722,983 A | 3/1998 | Van Der Weegen |
| 5,728,109 A | 3/1998 | Schulze et al. |
| 5,738,629 A | 4/1998 | Moll et al. |
| 5,743,852 A | 4/1998 | Johnson |
| 5,746,753 A | 5/1998 | Sullivan et al. |
| 5,749,883 A | 5/1998 | Halpern |
| 5,759,188 A | 6/1998 | Yoon |
| 5,766,183 A | 6/1998 | Sauer |
| 5,766,220 A | 6/1998 | Moenning |
| 5,769,870 A | 6/1998 | Salahieh et al. |
| 5,779,719 A | 7/1998 | Klein et al. |
| 5,792,152 A | 8/1998 | Klein et al. |
| 5,792,153 A | 8/1998 | Swain et al. |
| 5,795,289 A | 8/1998 | Wyttenbach |
| 5,795,325 A | 8/1998 | Valley et al. |
| 5,797,948 A | 8/1998 | Dunham |
| 5,797,960 A | 8/1998 | Stevens et al. |
| 5,810,757 A | 9/1998 | Sweezer et al. |
| 5,810,849 A | 9/1998 | Kontos |
| 5,810,850 A | 9/1998 | Hathaway et al. |
| 5,817,110 A | 10/1998 | Kronner |
| 5,820,631 A | 10/1998 | Nobles |
| 5,836,955 A | 11/1998 | Buelna et al. |
| 5,843,100 A | 12/1998 | Meade |
| 5,846,251 A | 12/1998 | Hart |
| 5,846,253 A | 12/1998 | Buelna et al. |
| 5,853,399 A | 12/1998 | Sasaki |
| 5,853,422 A | 12/1998 | Huebsch et al. |
| 5,855,585 A | 1/1999 | Kontos |
| 5,860,990 A | 1/1999 | Nobles et al. |
| 5,860,991 A | 1/1999 | Klein et al. |
| 5,860,992 A | 1/1999 | Daniel et al. |
| 5,860,997 A | 1/1999 | Bonutti |
| 5,861,003 A | 1/1999 | Latson et al. |
| 5,865,729 A | 2/1999 | Meehan et al. |
| 5,868,708 A | 2/1999 | Hart et al. |
| 5,868,762 A | 2/1999 | Cragg et al. |
| 5,871,537 A | 2/1999 | Holman et al. |
| 5,876,411 A | 3/1999 | Kontos |
| 5,899,921 A | 5/1999 | Caspari et al. |
| 5,902,311 A | 5/1999 | Andreas et al. |
| 5,902,321 A | 5/1999 | Caspari et al. |
| 5,906,577 A | 5/1999 | Beane et al. |
| 5,908,428 A | 6/1999 | Scirica et al. |
| 5,919,200 A | 7/1999 | Stambaugh et al. |
| 5,919,208 A | 7/1999 | Valenti |
| 5,928,192 A | 7/1999 | Maahs |
| 5,931,844 A | 8/1999 | Thompson et al. |
| 5,935,098 A | 8/1999 | Blaisdell et al. |
| 5,935,149 A | 8/1999 | Ek |
| 5,944,730 A | 8/1999 | Nobles et al. |
| 5,951,588 A | 9/1999 | Moenning |
| 5,951,590 A | 9/1999 | Goldfarb |
| 5,954,732 A | 9/1999 | Hart et al. |
| 5,967,970 A | 10/1999 | Cowan et al. |
| 5,971,983 A | 10/1999 | Lesh |
| 5,972,005 A | 10/1999 | Stalker et al. |
| 5,980,539 A | 11/1999 | Kontos |

(56) References Cited

U.S. PATENT DOCUMENTS

| | | |
|---|---|---|
| 5,993,466 A | 11/1999 | Yoon |
| 5,997,555 A | 12/1999 | Kontos |
| 6,001,109 A | 12/1999 | Kontos |
| 6,004,337 A | 12/1999 | Kieturakis et al. |
| 6,010,530 A | 1/2000 | Goicoechea |
| 6,015,428 A | 1/2000 | Pagedas |
| 6,024,747 A | 2/2000 | Kontos |
| 6,033,430 A | 3/2000 | Bonutti |
| 6,036,699 A | 3/2000 | Andreas et al. |
| 6,059,800 A | 5/2000 | Hart et al. |
| 6,066,160 A | 5/2000 | Colvin et al. |
| 6,068,648 A | 5/2000 | Cole et al. |
| 6,071,271 A | 6/2000 | Baker et al. |
| 6,077,277 A | 6/2000 | Mollenauer et al. |
| 6,086,608 A | 7/2000 | Ek et al. |
| 6,099,553 A | 8/2000 | Hart et al. |
| 6,110,185 A | 8/2000 | Barra et al. |
| 6,113,580 A | 9/2000 | Dolisi |
| 6,117,144 A | 9/2000 | Nobles et al. |
| 6,126,677 A | 10/2000 | Ganaja et al. |
| 6,136,010 A | 10/2000 | Modesitt et al. |
| 6,143,015 A | 11/2000 | Nobles |
| 6,159,234 A | 12/2000 | Bonutti et al. |
| 6,171,319 B1 | 1/2001 | Nobles et al. |
| 6,174,324 B1 | 1/2001 | Egan et al. |
| 6,187,026 B1 | 2/2001 | Devlin et al. |
| 6,190,396 B1 | 2/2001 | Whitin et al. |
| 6,200,329 B1 | 3/2001 | Fung et al. |
| 6,203,565 B1 | 3/2001 | Bonutti et al. |
| 6,210,429 B1 | 4/2001 | Vardi et al. |
| 6,217,591 B1 | 4/2001 | Egan et al. |
| 6,241,699 B1 | 6/2001 | Suresh et al. |
| 6,245,079 B1 | 6/2001 | Nobles et al. |
| 6,245,080 B1 | 6/2001 | Levinson |
| 6,248,121 B1 | 6/2001 | Nobles |
| 6,280,460 B1 | 8/2001 | Bolduc et al. |
| 6,290,674 B1 | 9/2001 | Roue et al. |
| 6,332,889 B1 | 12/2001 | Sancoff et al. |
| 6,348,059 B1 | 2/2002 | Hathaway et al. |
| 6,383,208 B1 | 5/2002 | Sancoff et al. |
| 6,409,739 B1 | 6/2002 | Nobles et al. |
| 6,432,115 B1 | 8/2002 | Mollenauer et al. |
| 6,468,293 B2 | 10/2002 | Bonutti et al. |
| 6,508,777 B1 | 1/2003 | Macoviak et al. |
| 6,527,785 B2 | 3/2003 | Sancoff et al. |
| 6,533,795 B1 | 3/2003 | Tran et al. |
| 6,537,299 B1 | 3/2003 | Hogendijk et al. |
| 6,547,725 B1 | 4/2003 | Paolitto et al. |
| 6,547,760 B1 | 4/2003 | Samson et al. |
| 6,551,331 B2 | 4/2003 | Nobles et al. |
| 6,562,052 B2 | 5/2003 | Nobles et al. |
| 6,585,689 B1 | 7/2003 | Macoviak et al. |
| 6,663,643 B2 | 12/2003 | Field et al. |
| 6,679,895 B1 | 1/2004 | Sancoff et al. |
| 6,682,540 B1 | 1/2004 | Sancoff et al. |
| 6,716,243 B1 | 4/2004 | Colvin et al. |
| 6,726,651 B1 | 4/2004 | Robinson et al. |
| 6,733,509 B2 | 5/2004 | Nobles et al. |
| 6,767,352 B2 | 7/2004 | Field et al. |
| 6,770,076 B2 | 8/2004 | Foerster |
| 6,786,913 B1 | 9/2004 | Sancoff |
| 6,855,157 B2 | 2/2005 | Foerster et al. |
| 6,893,448 B2 | 5/2005 | O'Quinn et al. |
| 6,911,034 B2 | 6/2005 | Nobles et al. |
| 6,913,600 B2 | 7/2005 | Valley et al. |
| 6,936,057 B1 | 8/2005 | Nobles |
| 6,978,176 B2 | 12/2005 | Lattouf |
| 7,004,952 B2 | 2/2006 | Nobles et al. |
| 7,083,630 B2 | 8/2006 | DeVries et al. |
| 7,083,638 B2 | 8/2006 | Foerster |
| 7,090,686 B2 | 8/2006 | Nobles et al. |
| 7,090,690 B2 | 8/2006 | Foerster et al. |
| 7,118,583 B2 | 10/2006 | O'Quinn et al. |
| 7,160,309 B2 | 1/2007 | Voss |
| 7,172,595 B1 | 2/2007 | Goble |
| 7,220,266 B2 | 5/2007 | Gambale |
| 7,232,446 B1 | 6/2007 | Farris |
| 7,235,086 B2 | 6/2007 | Sauer et al. |
| 7,326,221 B2 | 2/2008 | Sakamoto et al. |
| 7,329,272 B2 | 2/2008 | Burkhart et al. |
| 7,381,210 B2 | 6/2008 | Zarbatany et al. |
| 7,399,304 B2 | 7/2008 | Gambale et al. |
| 7,435,251 B2 | 10/2008 | Green |
| 7,449,024 B2 | 11/2008 | Stafford |
| 7,491,217 B1 | 2/2009 | Hendren |
| 7,601,161 B1 | 10/2009 | Nobles et al. |
| 7,628,797 B2 | 12/2009 | Tieu et al. |
| 7,635,386 B1 | 12/2009 | Gammie |
| 7,637,926 B2 | 12/2009 | Foerster et al. |
| 7,722,629 B2 | 5/2010 | Chambers |
| 7,803,167 B2 | 9/2010 | Nobles et al. |
| 7,842,051 B2 | 11/2010 | Dana et al. |
| 7,846,181 B2 | 12/2010 | Schwartz et al. |
| 7,879,072 B2 | 2/2011 | Bonutti et al. |
| 7,905,892 B2 | 3/2011 | Nobles et al. |
| 7,918,867 B2 | 4/2011 | Dana et al. |
| 7,993,368 B2 | 8/2011 | Gambale et al. |
| 8,075,573 B2 | 12/2011 | Gambale et al. |
| 8,083,754 B2 | 12/2011 | Pantages et al. |
| 8,105,355 B2 | 1/2012 | Page et al. |
| 8,197,497 B2 | 6/2012 | Nobles et al. |
| 8,246,636 B2 | 8/2012 | Nobles et al. |
| 8,252,005 B2 | 8/2012 | Findlay, III et al. |
| 8,282,659 B2 | 10/2012 | Oren et al. |
| 8,287,556 B2 | 10/2012 | Gilkey et al. |
| 8,298,291 B2 | 10/2012 | Ewers et al. |
| 8,303,622 B2 | 11/2012 | Alkhatib |
| 8,348,962 B2 | 1/2013 | Nobles et al. |
| 8,372,089 B2 | 2/2013 | Nobles et al. |
| 8,469,975 B2 | 6/2013 | Nobles et al. |
| 8,496,676 B2 | 7/2013 | Nobles et al. |
| 8,540,736 B2 | 9/2013 | Gaynor et al. |
| 8,568,427 B2 | 10/2013 | Nobles et al. |
| 8,758,370 B2 | 6/2014 | Shikhman et al. |
| 8,771,296 B2 | 7/2014 | Nobles et al. |
| 9,131,938 B2 | 9/2015 | Nobles et al. |
| 9,326,764 B2 | 5/2016 | Nobles et al. |
| 9,398,907 B2 | 7/2016 | Nobles et al. |
| 2001/0031973 A1 | 10/2001 | Nobles et al. |
| 2002/0013601 A1 | 1/2002 | Nobles et al. |
| 2002/0045908 A1 | 4/2002 | Nobles et al. |
| 2002/0049453 A1 | 4/2002 | Nobles et al. |
| 2002/0087178 A1 | 7/2002 | Nobles et al. |
| 2002/0096183 A1 | 7/2002 | Stevens et al. |
| 2002/0111653 A1 | 8/2002 | Foerster |
| 2002/0128598 A1 | 9/2002 | Nobles |
| 2002/0128684 A1 | 9/2002 | Foerster |
| 2003/0078601 A1 | 4/2003 | Shikhman et al. |
| 2003/0144673 A1 | 7/2003 | Onuki et al. |
| 2003/0149448 A1 | 8/2003 | Foerster et al. |
| 2003/0167062 A1 | 9/2003 | Gambale et al. |
| 2003/0171760 A1 | 9/2003 | Gambale |
| 2003/0181926 A1 | 9/2003 | Dana et al. |
| 2003/0208209 A1 | 11/2003 | Gambale et al. |
| 2004/0044365 A1 | 3/2004 | Bachman |
| 2004/0059351 A1 | 3/2004 | Eigler et al. |
| 2004/0093031 A1 | 5/2004 | Burkhart et al. |
| 2004/0097968 A1 | 5/2004 | Shikhman et al. |
| 2004/0098050 A1 | 5/2004 | Foerster et al. |
| 2004/0153116 A1 | 8/2004 | Nobles |
| 2004/0210238 A1 | 10/2004 | Nobles et al. |
| 2004/0236356 A1 | 11/2004 | Rioux et al. |
| 2004/0260298 A1 | 12/2004 | Kaiser et al. |
| 2005/0033319 A1 | 2/2005 | Gambale et al. |
| 2005/0070923 A1 | 3/2005 | McIntosh |
| 2005/0149066 A1 | 7/2005 | Stafford |
| 2005/0187575 A1* | 8/2005 | Hallbeck ............ A61B 17/29 606/205 |
| 2005/0203564 A1 | 9/2005 | Nobles |
| 2005/0240226 A1 | 10/2005 | Foerster et al. |
| 2005/0261708 A1 | 11/2005 | Pasricha et al. |
| 2005/0261710 A1 | 11/2005 | Sakamoto et al. |
| 2005/0277986 A1 | 12/2005 | Foerster et al. |
| 2005/0288688 A1 | 12/2005 | Sakamoto et al. |

(56) References Cited

U.S. PATENT DOCUMENTS

| | | |
|---|---|---|
| 2006/0047314 A1 | 3/2006 | Green |
| 2006/0052813 A1 | 3/2006 | Nobles |
| 2006/0064115 A1 | 3/2006 | Allen et al. |
| 2006/0069397 A1 | 3/2006 | Nobles et al. |
| 2006/0074484 A1 | 4/2006 | Huber |
| 2006/0095052 A1 | 5/2006 | Chambers |
| 2006/0195120 A1 | 8/2006 | Nobles et al. |
| 2006/0265010 A1 | 11/2006 | Paraschac et al. |
| 2006/0271074 A1 | 11/2006 | Ewers et al. |
| 2006/0282088 A1 | 12/2006 | Ryan |
| 2006/0282102 A1 | 12/2006 | Nobles et al. |
| 2006/0287657 A1 | 12/2006 | Bachman |
| 2007/0005081 A1 | 1/2007 | Findlay et al. |
| 2007/0010829 A1 | 1/2007 | Nobles et al. |
| 2007/0032798 A1 | 2/2007 | Pantages et al. |
| 2007/0043385 A1 | 2/2007 | Nobles et al. |
| 2007/0118151 A1 | 5/2007 | Davidson |
| 2007/0213757 A1 | 9/2007 | Boraiah |
| 2007/0219630 A1 | 9/2007 | Chu |
| 2007/0276413 A1 | 11/2007 | Nobles |
| 2007/0276414 A1 | 11/2007 | Nobles |
| 2008/0033459 A1 | 2/2008 | Shafi et al. |
| 2008/0077162 A1 | 3/2008 | Domingo |
| 2008/0188873 A1 | 8/2008 | Speziali |
| 2008/0228201 A1 | 9/2008 | Zarbatany |
| 2008/0234729 A1 | 9/2008 | Page et al. |
| 2008/0269786 A1 | 10/2008 | Nobles et al. |
| 2009/0036906 A1 | 2/2009 | Stafford |
| 2009/0048615 A1 | 2/2009 | McIntosh |
| 2009/0105729 A1 | 4/2009 | Zentgraf |
| 2009/0105751 A1 | 4/2009 | Zentgraf |
| 2009/0118726 A1 | 5/2009 | Auth et al. |
| 2009/0287183 A1 | 11/2009 | Bishop et al. |
| 2010/0016870 A1 | 1/2010 | Campbell |
| 2010/0030242 A1 | 2/2010 | Nobles et al. |
| 2010/0042147 A1 | 2/2010 | Janovsky et al. |
| 2010/0087838 A1 | 4/2010 | Nobles et al. |
| 2011/0190793 A1 | 8/2011 | Nobles et al. |
| 2011/0251627 A1 | 10/2011 | Hamilton et al. |
| 2012/0016384 A1 | 1/2012 | Wilke et al. |
| 2012/0165838 A1 | 6/2012 | Kobylewski et al. |
| 2014/0148825 A1 | 5/2014 | Nobles et al. |
| 2015/0126815 A1 | 5/2015 | Nobles |
| 2015/0374351 A1 | 12/2015 | Nobles et al. |
| 2016/0007998 A1 | 1/2016 | Nobles et al. |
| 2016/0151064 A1 | 6/2016 | Nobles |
| 2016/0302787 A1 | 10/2016 | Nobles |

FOREIGN PATENT DOCUMENTS

| | | |
|---|---|---|
| CN | 101257852 | 8/2011 |
| CN | 103889345 B | 10/2016 |
| DE | 29 01 701 | 7/1980 |
| EP | 0 241 038 | 10/1987 |
| EP | 0 544 485 | 6/1993 |
| EP | 0839 550 | 5/1998 |
| EP | 0 894 475 | 2/1999 |
| EP | 1 196 093 | 4/2002 |
| EP | 1 303 218 | 4/2003 |
| EP | 0 941 698 | 5/2005 |
| EP | 0 983 027 | 12/2005 |
| FR | 2 701 401 | 8/1994 |
| JP | A 9507398 | 7/1997 |
| JP | 09-266910 A | 10/1997 |
| JP | H10-43192 | 2/1998 |
| JP | 2001-524864 | 12/2001 |
| JP | 2007-503870 | 3/2007 |
| JP | 2008-514305 | 5/2008 |
| JP | 2008-541857 | 11/2008 |
| JP | 2008-546454 | 12/2008 |
| JP | 2009-261960 | 11/2009 |
| JP | 2010-522625 | 7/2010 |
| JP | 5848125 | 12/2015 |
| SU | 1560129 A1 | 4/1990 |
| WO | WO 92/05828 | 4/1992 |
| WO | WO 93/01750 | 2/1993 |
| WO | WO 93/07800 | 4/1993 |
| WO | WO 95/12429 | 5/1995 |
| WO | WO 95/17127 | 6/1995 |
| WO | WO 95/25468 | 9/1995 |
| WO | WO 95/25470 A1 | 9/1995 |
| WO | WO 96/03083 | 2/1996 |
| WO | WO 96/29012 | 9/1996 |
| WO | WO 96/40347 | 12/1996 |
| WO | WO 97/03613 | 2/1997 |
| WO | WO 97/47261 | 2/1997 |
| WO | WO 97/07745 | 3/1997 |
| WO | WO 97/12540 | 4/1997 |
| WO | WO 97/20505 | 6/1997 |
| WO | WO 97/24975 | 7/1997 |
| WO | WO 97/27807 | 8/1997 |
| WO | WO 97/40738 | 11/1997 |
| WO | WO 98/12970 A1 | 4/1998 |
| WO | WO 98/52476 | 11/1998 |
| WO | WO 99/40851 | 8/1999 |
| WO | WO 99/42160 | 8/1999 |
| WO | WO 99/45848 | 9/1999 |
| WO | WO 00/02489 A1 | 1/2000 |
| WO | WO 01/01868 | 1/2001 |
| WO | WO 01/95809 | 12/2001 |
| WO | WO 02/24078 | 3/2002 |
| WO | WO 2004/012789 | 2/2004 |
| WO | WO 2006/127636 | 11/2006 |
| WO | WO 2007/001936 | 1/2007 |
| WO | WO 2009/081396 | 7/2009 |
| WO | WO 2011/094619 | 8/2011 |
| WO | WO 2015/002815 | 1/2015 |
| WO | WO 2015/085145 | 6/2015 |

OTHER PUBLICATIONS

Written Opinion on Patentability dated Jun. 6, 2007 for International Application No. PCT/US2006/023676, 7 pages.

International Search Report dated Jun. 6, 2007 for International Application No. PCT/US2006/023676, 1 page.

International Search Report and Written Opinion, dated Jun. 6, 2007 for International Application No. PCT/US2006/023676, in 14 pages.

U.S. Appl. No. 09/080,823, filed May 18, 1998, Nobles.

U.S. Appl. No. 09/080,436, filed May 18, 1999, Nobles.

U.S. Appl. No. 13/736,032, filed Jan. 7, 2013, Nobles et al.

U.S. Appl. No. 14/850,210, filed Sep. 10, 2015, Nobles et al.

U.S. Appl. No. 15/215,960, filed Jul. 21, 2016, Nobles et al.

Advances in Vascular Surgery, by John S. Najarian, M.D. and John P. Delaney, M.D., copyright 1983 by Year Book Publishers, Inc. at pp. 94,95,96, and 224.

Cardio Medical Solutions, Inc. brochure titled: "Baladi Inverter for Clamp less Surgery" —Undated.

Clinical Evaluation of Arteriovenous Fistulas as an Adjunct to Lower Extremity Arterial Reconstructions, by Herbert Dardick, M.D., in Current Critical Problems in Vascular Surgery, copyright 1989 by Quality Medical Publishing Inc., at p. 383.

Current Therapy in Vascular Surgery, 2nd edition, by Calvin B. Ernst, M.D. and James C. Stanley, M.D., copyright 1991 by B.C. Decker, Inc., at pp. A and 140.

Eskuri, A., The Design of a Minimally Invasive Vascular Suturing Device, Thesis submitted to Rose-Hulman Institute of Technology, Nov. 1999.

Manual of Vascular Surgery, vol. 2, Edwin J. Wylie, Ronald J. Stoney, William K. Ehrenfeld and David J. Effeney (Richard H. Egdahl ed.), copyright 1986 by Springer-Verlag New York Inc., at p. 41.

Nursing the Open-Heart Surgery Patient, by Mary Jo Aspinall, R.N., M.N., copyright 1973 by McGraw Hill, Inc., at pp. 216 and 231.

Operative Arterial Surgery, by P.R. Bell, M.D., and W Barrie, M.D., copyright 1981 by Bell, Barrie, and Leicester Royal Infirmary, printed byJohn Wright &Sons, pp. 16, 17, 104, 105, 112, and 113.

Sinus Venous Type of Atrial Septal Defect with Partial Anomalous Pulmonary Venous Return, by Francis Robicsek, MD., et ai, in Journal of Thoracic and Cardiovascular Surgery, Oct. 1979, vol. 78, No. 4, at pp. 559-562.

(56) References Cited

OTHER PUBLICATIONS

Techniques in Vascular Surgery, by Denton A. Cooley, MD. and Don C. Wukasch, MD., copyright 1979 by WB. Saunders Co., at pp. 38,57,86,134,156, and 184.
The problem: Closing wounds in deep areas during laparoscopic operations The solution: REMA Medizintechnik GmbH (no date).
Vascular Access, Principles and Practice, 3rd edition, by Samuel Eric Wilson, MD., copyright 1996, 1988,1980 by Mosby-Year Book, Inc., pp. 89 and 159.
Vascular and Endovascular Surgery, by Jonathan D. Beard and Peter Gainers, copyright 1998 by W. B. Saunders Co., Ltd, p. 414.
Vascular Surgery, 3rd edition, vol. 1, by Robert B. Rutherford, MD., copyright 1989, 1984, 1976 by W. B.SaundersCo., at pp. 347, 348, 354, 594, 607, 622, 675, 677, 680, 698, 700, 721, 727, 735, and 829.
Vascular Surgery, 4th edition by Robert B. Rutherford, MD., copyright 1995, 1989, 1976, by W.B. Saunders Co., vol. 1, at pp. 400-404, 661, and A.
Vascular Surgery, 4th edition, by Robert B. Rutherford, M.D., copyright 1995, 1989, 1984, 1976 by W. B. Saunders Co., vol. 2, at pp. 1318, 1363, 1426, 1564, and 1580.
Vascular Surgery, by Robert B. Rutherford, M.D. copyright1977 by WB. Saunders Co., at pp. 334 and 817.

\* cited by examiner

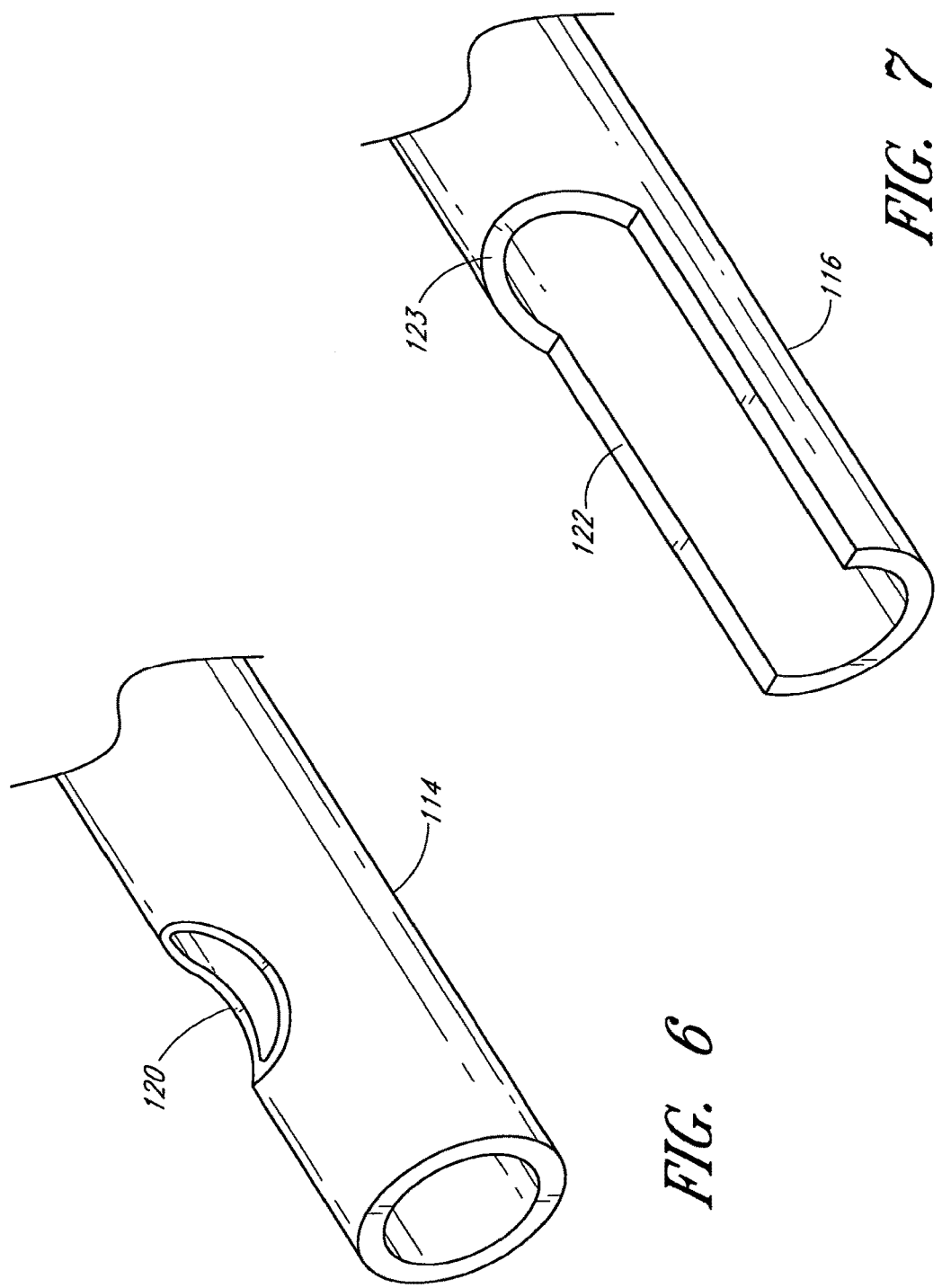

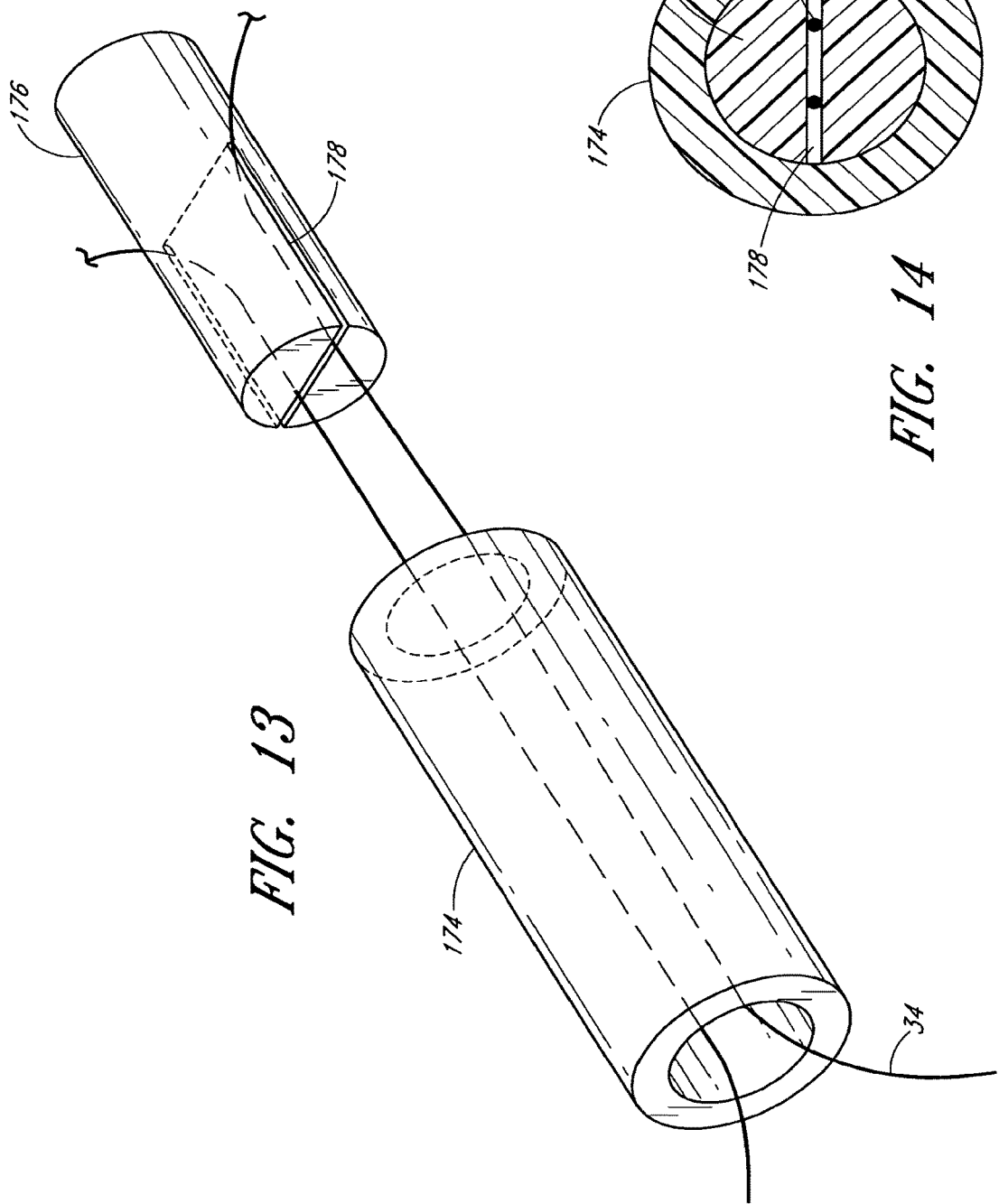

METHOD AND APPARATUS FOR APPLYING A KNOT TO A SUTURE

CROSS-REFERENCE TO RELATED APPLICATIONS

This application is a continuation of Ser. No. 13/489,573 filed Jun. 6, 2012; which is a division of U.S. application Ser. No. 11/455,894, filed on Jun. 19, 2006, now U.S. Pat. No. 8,197,497, which claims the benefit of U.S. Provisional Application No. 60/693,582, filed on Jun, 20, 2005 and U.S. Provisional Application No. 60/009,485, filed on Aug. 19, 2005, the entirety of which are hereby incorporated by reference.

BACKGROUND OF THE INVENTION

1. Field of the Invention

Certain embodiments of the invention relate to suturing incisions and, more specifically, to the use of sutures for closing incisions in vessels or in organs within a body.

2. Description of the Related Art

Surgeons frequently encounter the need to close incisions, wounds, or otherwise joining tissue portions with a suture. After passing the suture through the tissue portions, the surgeon must tie and cinch the suture to draw the tissue portions together and prevent them from separating. When sutures are tied in a region having restricted access, such as the end of a tissue tract leading to an artery, the surgeon is presented with special challenges. Sutures can often be difficult to handle, thereby increasing the time that it takes for a surgeon to tie a suture. Accordingly, what is needed is a faster and more effective way to tie and cinch a suture.

SUMMARY OF THE INVENTION

Certain embodiments of the present invention describe various methods and apparatus for applying a knot to a suture. When two ends of a suture extend away from an incision in a vessel or an organ of a patient, the preferred embodiments provide a method and apparatus for desirably securing two suture portions relative to each other, with the securement being provided adjacent the incision to hold the incision closed. As used herein, the term "knot" is a broad term encompassing its ordinary meaning and includes, but is not limited to, any arrangement, component or combination of components designed to fixedly hold a suture relative to a desired knot location. More preferably, a knot may encompass any arrangement, component or combination of components designed to fixedly hold two portions of a suture relative to a desired knot location. Thus, a knot encompasses arrangements in which suture portions are tied, and also encompasses arrangements in which suture portions are securely held relative to one another without being tied. The desired knot location may include an incision, a wound, a body cavity, an opening in body tissue, and two adjacent body tissues wherein the space between the two adjacent body tissues is desired to be closed. The two suture portions may be portions of the same suture or different sutures.

In one embodiment, a knot placement device is provided. The knot placement device preferably includes a handle and a shaft. The handle comprises a proximal end and a distal end. The shaft comprises a proximal end and a distal end which extends distally from the handle. A knot is disposed, either partially or entirely, within the distal end of the shaft. The handle further comprises an actuator which places the knot about two suture portions to fix the two suture portions relative to one another.

In one embodiment, the actuator may be a thumb or finger button designed for cooperation with a cam. The cam may be fixedly attached to a push rod. The push rod is concentrically and slidably disposed within an outer tube. The outer tube may be fixedly attached to a distal end portion of the handle. The knot placement device may further comprise an intermediate tube concentrically and slidably disposed between the outer tube and the push rod. The intermediate tube comprises a proximal end and a distal end. The proximal end of the intermediate tube may be located between the cam and the distal end portion of the handle. Partial depression of the actuator distally advances the push rod. At some degree of depression, the actuator contacts the proximal end of the intermediate tube, thus distally advancing the intermediate tube.

In one embodiment, the intermediate tube may comprise a key. The outer tube, the end portion, or both may include a keyway designed for cooperation with the key. The key and associated keyway maintain rotational alignment of the intermediate tube relative to the outer tube. In another embodiment, the intermediate tube may comprise a keyway, and the outer tube or the end portion may comprise a key.

In one embodiment, the shaft comprises an outer tube having a proximal end and a distal end. The outer tube may comprise an aperture located near its distal end. The shaft may further comprise an intermediate tube concentrically and slidably disposed within the outer tube. The intermediate tube may comprise a slot located at or near its distal end. A push rod may be concentrically and slidably disposed within the intermediate tube and outer tube. A knot is disposed, either partially or entirely, within the distal end of the outer tube.

In one embodiment, the knot comprises a plug and a knot body, wherein the plug is adapted to be received within the knot body. The plug comprises a proximal end and a distal end, and may be of a generally constant outer diameter. Alternatively, the plug may be generally tapered from the proximal end to the distal end. Alternatively, the plug may comprise a portion of generally constant outer diameter and a generally tapered portion. The plug may also comprise a rounded or chamfered edge at the distal end. The plug may also comprise a shoulder located near the proximal end having an increased outer diameter.

The knot body may be generally tubular and comprise a proximal end, a distal end, and a longitudinal axis. The knot body may be of a generally constant inner diameter and outer diameter. Alternatively, the inner diameter, the outer diameter, or both may generally taper along the longitudinal axis of the knot body. Alternatively, the inner diameter, the outer diameter, or both may generally taper along a portion of the longitudinal axis and may be of a generally constant inner diameter, outer diameter or both over a portion of the longitudinal axis.

The knot body may comprise an opening at its distal end. The opening at the distal end of the knot body may, in some embodiments, be of a reduced diameter. The knot body may also comprise an opening at the proximal end. The opening at the proximal end may, in some embodiments, be of a reduced diameter. The knot body may further comprise protrusions from the inner surface of the knot body toward the longitudinal axis.

In one embodiment, the knot body may be located distally from the plug within the outer tube. In another embodiment, the plug may be located distally from the knot body within the outer tube.

In one embodiment, a method is provided for placing a knot on a suture to close an opening in the body. A pair of suture ends is passed through a threader. The threader is pulled through a passage in the distal end of a shaft of a knot placement device. As the threader is pulled through the passage, the suture portions are drawn through the passage, and desirably positioned within a knot body positioned at a distal end of the shaft. Tension may be applied to the suture portions as the knot placement device is slid along the suture portions toward a pair of tissue portions. The knot placement device is advanced until the knot body or distal end of the device is in contact with a tissue portion. An actuator is depressed, which in one embodiment advances a push rod within the shaft against a plug and advances the plug into the knot body. This traps the suture between the plug and the knot body. In one preferred embodiment, continued depression of the actuator causes an intermediate tube to be advanced to sever the suture portions, eject the knot from the placement device, or both. The device is then retracted from the patient.

In one embodiment, after the knot is ejected and before the suture ends are severed, the push rod is positioned substantially flush with a distal end of the shaft. The distal end of the shaft is used to push the knot toward the tissue portions to further secure the knot and draw the tissue portions closer together.

BRIEF DESCRIPTION OF THE DRAWINGS

FIG. 6 is a perspective view of the distal end of the outer tube of the knot placement device of FIG. 2.

FIG. 7 is a perspective view of the distal end of the intermediate tube of the knot placement device of FIG. 2.

FIG. 13 is a perspective view of another embodiment of a knot.

FIG. 14 is a transverse cross-sectional view of the knot of FIG. 13.

FIG. 18b is a cross-sectional side view of the knot of FIG. 18a.

DETAILED DESCRIPTION OF THE PREFERRED EMBODIMENTS

The preferred embodiments of the present invention described below relate particularly to applying a knot to two portions of a suture. More particularly, the preferred embodiments relate to applying a knot to portions of a suture extending from a treatment location of a patient. The treatment location may be any desired location, such as an arterial vessel, a venous vessel, or any other body tissue. Suture ends may be the ends of the same suture or may be the ends of separate sutures.

Figure 1:
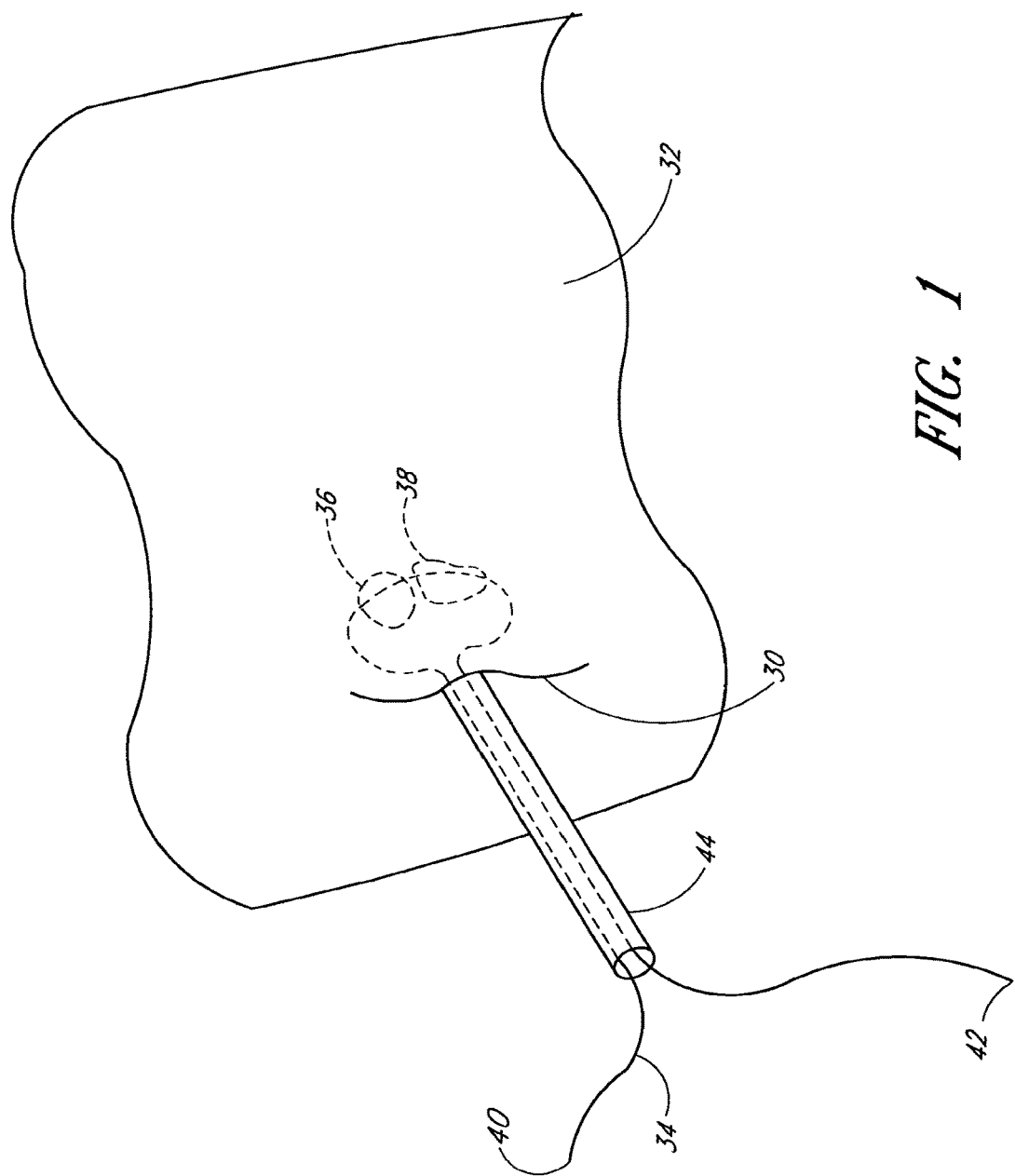
FIG. 1 is a perspective view of a wound site having a pair of suture ends extending therefrom.

FIG. 1 illustrates the wound site of a patient wherein it may be desired to apply a knot to a suture. More particularly, FIG. 1 shows an incision 30 in the patient's skin used to perform any sort of treatment on the patient. After the patient has been treated, a suture 34 is introduced into the patient through a catheter sheath introducer (CSI) 44 for the purpose of drawing together tissue portions 36 and 38 (shown in phantom in FIG. 1). Two end portions 40 and 42 of the suture 34 extend from the tissue portions 36, 38, respectively, which may, for example, be the result of a wound or an internal incision in a blood vessel or an organ. The suture 34 may be introduced into the patient by any suitable manner, including those described in U.S. Pat. Nos. 5,860,990, 6,117,144, 6,562,052, and Applicant's co-pending application Ser. No. 11/235,751 filed Sep. 27, 2005, now U.S. Publication No. 2006-0069397, all of which are hereby incorporated by reference in their entirety. Suture 34 may be, but is not limited to, 0.007" diameter biodegradable material or non-biodegradable materials, such as polypropylene. The suture 34 may also be braided or may be of other materials and have other configurations. The suture 34 in FIG. 1 is shown extending from a catheter sheath introducer 44. The suture 34 may also extend directly from an incision in a patient.

Figure 2:
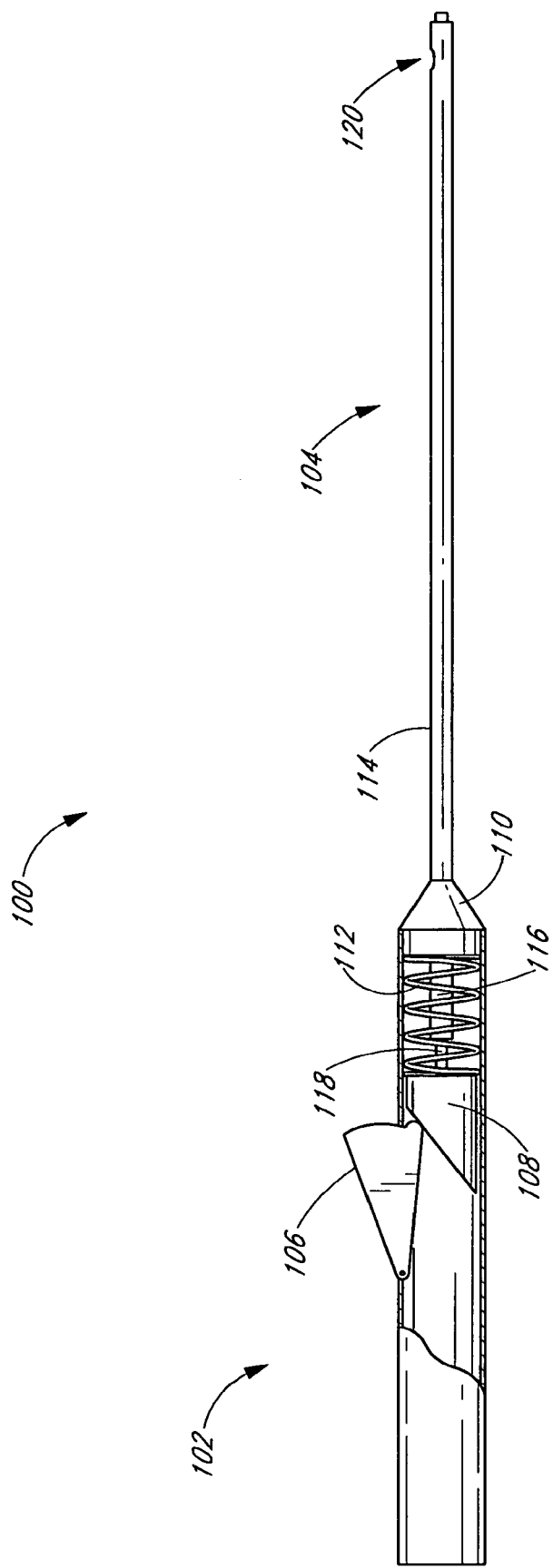
FIG. 2 is a side view of one embodiment of a knot placement device.
Figure 3:
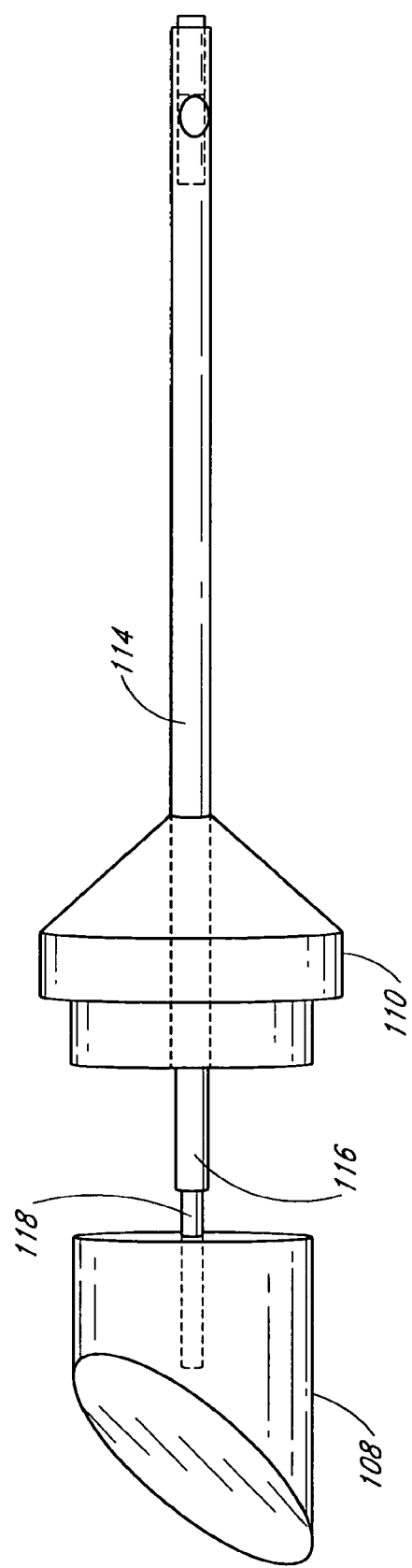
FIG. 3 is a side view of the shaft, cam, and distal end portion of the knot placement device of FIG. 2 with a knot shown within the shaft in phantom.
Figure 4:
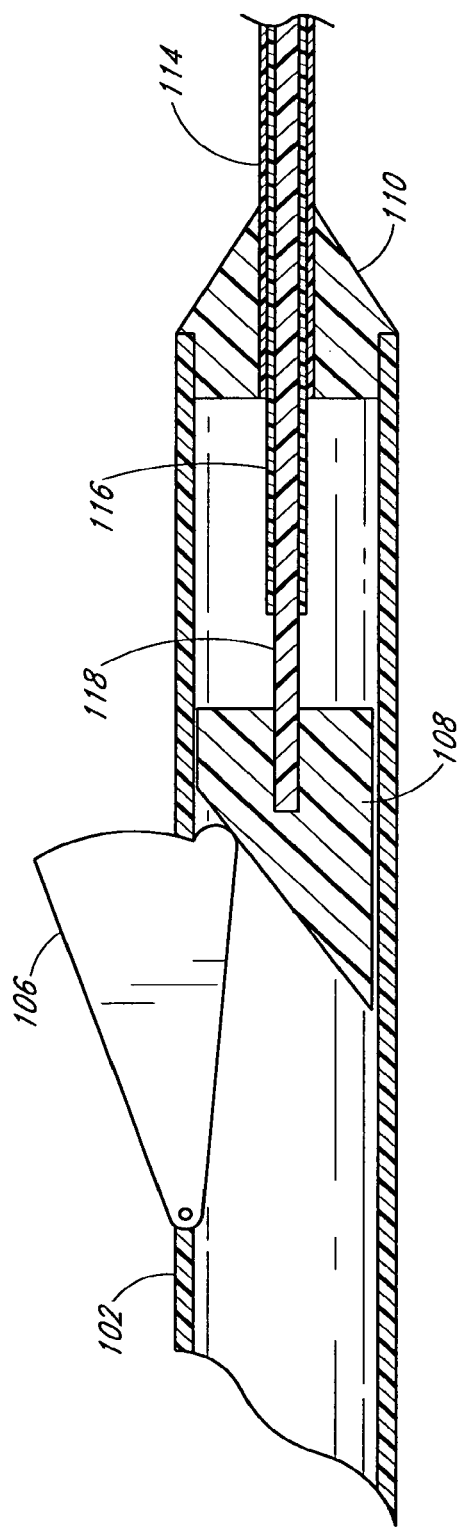
FIG. 4 is a partial cross-sectional side view of the handle of the knot placement device of FIG. 2.

FIGS. 2-4 illustrate one embodiment of a knot placement device 100 that may be used to apply a knot to the suture 34. The knot placement device 100 comprises a handle 102 and a shaft 104 extending distally from the handle. The handle 102 preferably comprises an elongate tubular body extending from a proximal end to a distal end, and comprises an actuator 106 and a distal end portion 110. The handle 102 may further comprise a cam 108 and a spring 112, shown in its rest position, disposed between the cam 108 and end portion 110. The actuator 106 may be a thumb or finger button in contact with the cam 108. End portion 110 may be fixedly attached to an outer tube 114 by glue, press fit, injection molding, or other suitable means know to one of ordinary skill in the art. An intermediate tube 116 may be concentrically and slidably disposed within the outer tube 114. A push rod 118 is concentrically and slidably disposed within the intermediate tube 116 and fixedly attached to the cam 108. It should be appreciated that it is contemplated that the knot placement device 100 does not necessarily comprise an intermediate tube 116; however its inclusion provides certain benefits.

As shown in FIG. 4, depression of the actuator 106 causes the cam 108 to move distally, compressing the spring 112 (not shown), thereby moving the push rod 108. After traveling for a certain desired distance, the cam 108 engages a proximal end of the intermediate tube 116, causing the intermediate tube 116 to also move distally. Upon release of the actuator 106, the spring 112 expands to move the cam 108 and the push rod 118 proximally. In the illustrated embodiment, the intermediate tube 116 is freely slidable over the push rod 118.

In one embodiment, not shown, the cam 108 comprises a detent in the surface which contacts the actuator 106. The detent may signal to the user a specific degree of advancement of the push rod 118, the intermediate tube 116, or both. For example, the detent may signal that the push rod has been advanced sufficiently far to insert the plug into the knot body, as described below. The detent may also indicate travel up until, but not including, the point at which the cam 108 engages the intermediate tube 116. The detent may be shaped so as to prevent the actuator 106 from returning to its original position. The cam may comprise multiple detents to indicate multiple increments of travel. To return the actuator to its initial position, the actuator and cam may include a mechanism such that after the actuator is fully depressed, the actuator may automatically return to its initial position. Alternatively, the actuator may have a locked configuration, either at one of the detents or in a fully depressed configuration, and the handle may include a mechanism by which a second actuator is used to release the cam and actuator to return to their initial positions. Further details of such mechanisms are found in application Ser. No. 11/235,751 filed Sep. 27, 2005, the entirety of which is hereby incorporated by reference.

In one embodiment, not shown, the intermediate tube 116 may comprise a keyway and the outer tube 114, the end portion 110, or both may comprise a key. Alternatively, the intermediate tube 116 may comprise a key and the outer tube 114, the end portion 110, or both may comprise a keyway. Providing such a key and keyway may be used to keep the intermediate tube 116 aligned with the outer tube. Other embodiments are contemplated to maintain rotational alignment of the intermediate tube, such as by rotationally fixing the intermediate tube relative to the push rod. Providing such a key and keyway may also be used to constrain the range of sliding movement of the intermediate tube 116.

Figure 5:
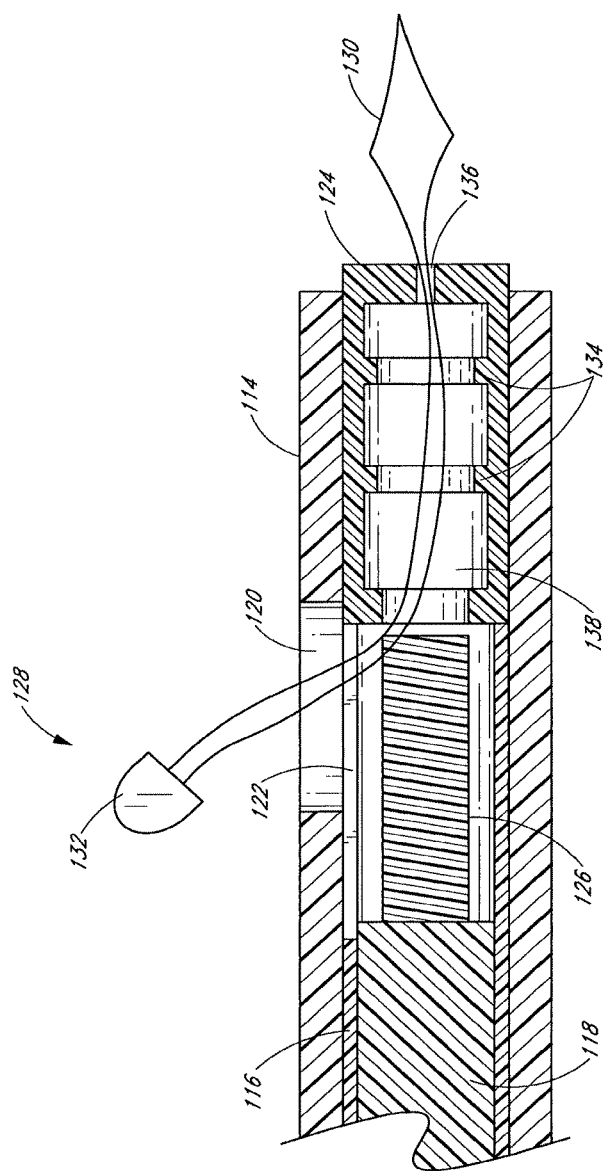
FIG. 5 is a partial cross-sectional side view of the distal end of the shaft of the knot placement device of FIG. 2.

As shown in FIG. 5, a knot, comprising a knot body 124 and a plug 126, is disposed within the outer tube 114 at its distal end. The knot body 124 may be retained in the outer tube 114 by a net fit or press fit. Alternatively, the fit between the knot body 124 and the outer tube 114 may not retain the knot body 124 in the outer tube 114. The knot body 124 is preferably at the distal end of the outer tube 114, and may protrude slightly distal to the distal end of outer tube 114. The plug 126 is positioned proximal to the knot body 124, and may be slidably disposed within the intermediate tube 116, having a distal end located proximally from the knot body and distally from the push rod 118. The plug 126 has an outer dimension configured to be inserted into an inner cavity of the knot body 124. The intermediate tube 116 is preferably sized and positioned such that its distal end may abut knot body 124.

Figure 8:
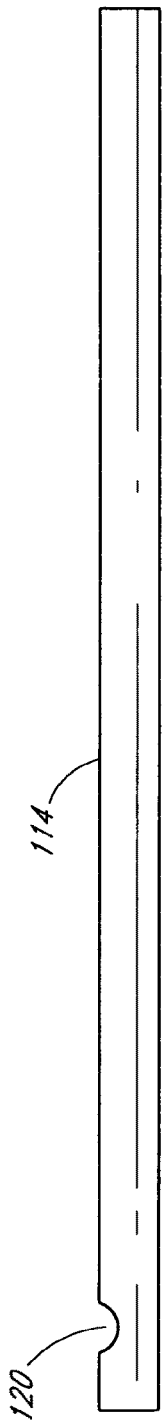
FIG. 8 is a side view of the outer tube of FIG. 6.
Figure 9A:
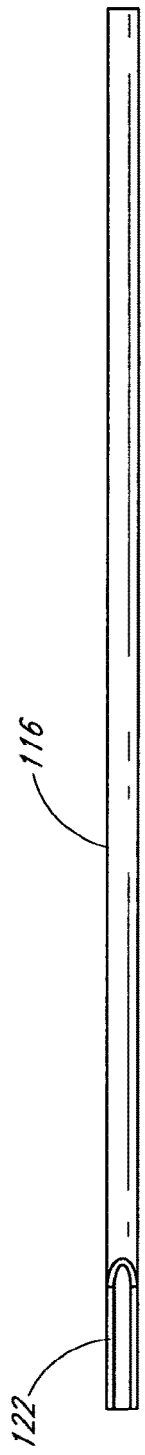
FIG. 9a is a top view of the intermediate tube of FIG. 7.
Figure 9B:
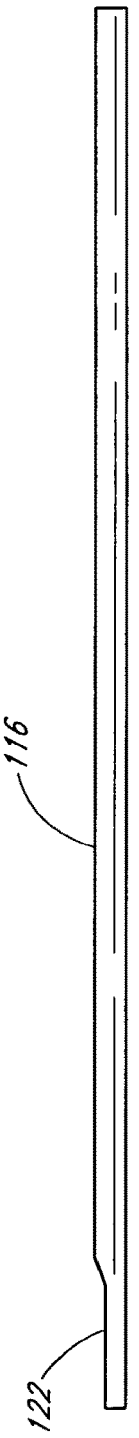
FIG. 9b is a side view of the intermediate tube of FIG. 7.

As shown in FIGS. 5, 6 and 8, the outer tube 114 may include a side hole 120 near its distal end. As shown in FIGS. 5, 7, 9a and 9b, the intermediate tube 116 may include a slot 122 extending proximally from its distal end, forming a C-shaped cross section. At a proximal end of the slot 122, a sharpened cutting surface 123 may be provided to cut suture 34, as described below. The slot 122 is preferably rotationally aligned with the opening 120, such as by using a key/keyway arrangement as described above. The slot 122 is also preferably axially aligned with the opening 120, although it will be appreciated that because of the ability of the intermediate tube 116 to slide relative to push rod 118, the intermediate tube may be positioned with the slot 122 proximal to the opening 120 and its distal end proximal to the plug 126. The slot 122 may also be spaced from the distal end of the intermediate tube, such that the distal end of the tube still forms a complete circle in cross-section. The outer tube 114, intermediate tube 116 and push rod 118 may be made of any suitable material, including but not limited to metals, plastics, and a combination of metals and plastics.

As shown in FIG. 5, in a preloaded configuration, the knot placement device 100 may include a threader 128 comprising a tab 132 and a looped wire 130 passing through the side hole 120 in the outer tube 114. The wire 130 preferably extends through the slot 122 located in the intermediate tube 116, and through knot body 124, exiting through opening 136 at the distal end of the knot body 124. The threader 128 is used to load the suture into the knot placement device as described below. The threader 128 also prevents the knot body 124 from escaping from the placement device 100 when the knot body is provided with an outer dimension of the same or smaller size than the inner wall of the outer tube 114.

Figure 10:
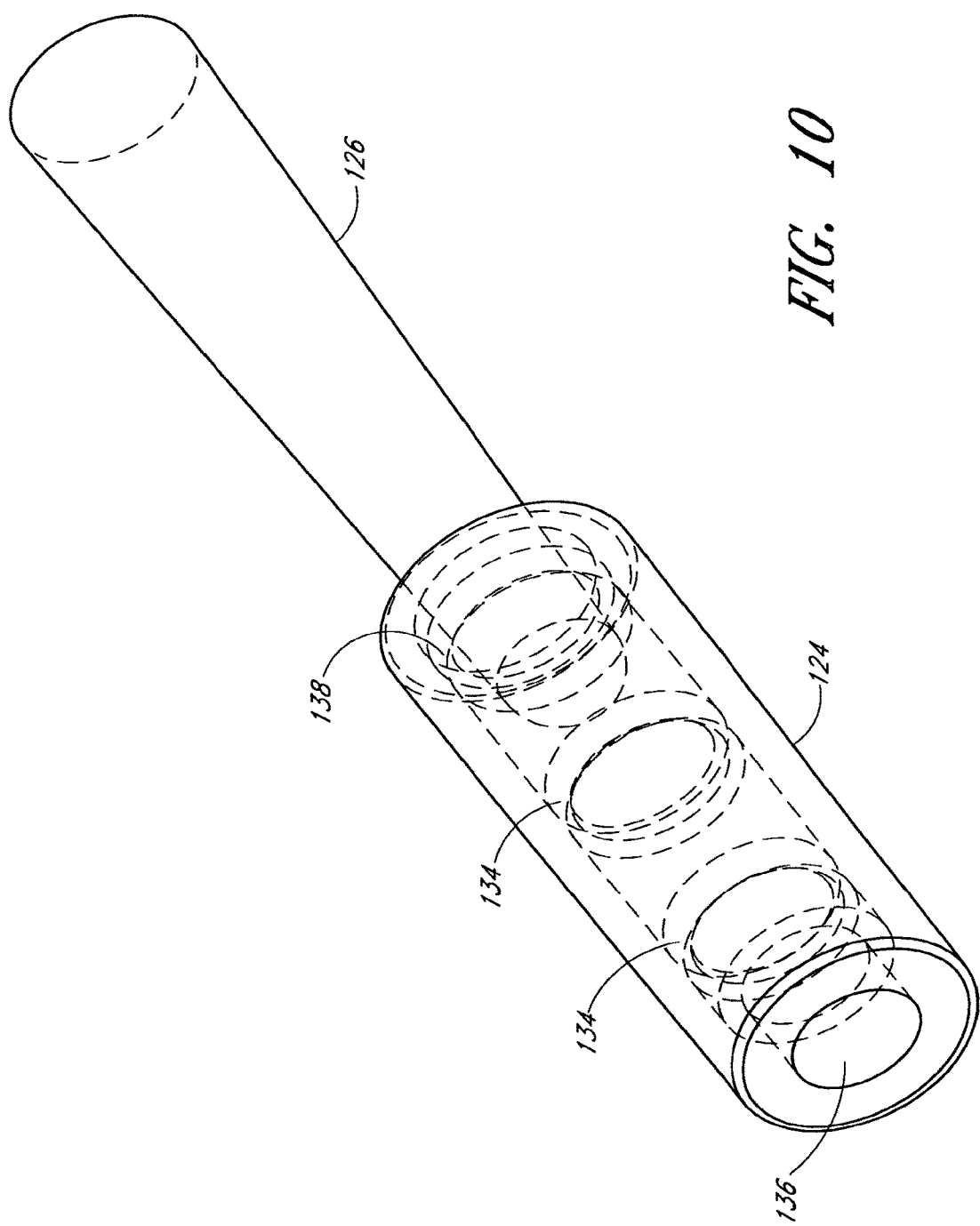
FIG. 10 is a perspective view of one embodiment of a knot.

With reference to FIGS. 5 and 10, the knot body 124 may be generally tubular and comprise a proximal end, a distal end, and a longitudinal axis. The knot body 124 preferably further defines an inner cavity and comprises an opening 136 at its distal end. The knot body may be of a generally constant inner diameter and outer diameter. Alternatively, the inner diameter, the outer diameter, or both may generally taper along the longitudinal axis of the knot body. Alternatively, the inner diameter, the outer diameter, or both may generally taper along a portion of the longitudinal axis and may be of a generally constant inner diameter, outer diameter or both over a portion of the longitudinal axis.

The opening 136 at the distal end of the knot body may, in some embodiments, be of a reduced diameter relative to an inner cavity of the knot body 124. The knot body also comprises an opening 138 at the proximal end. The opening 138 at the proximal end may, in some embodiments, be of a reduced diameter relative to an inner cavity of the knot body 124. The knot body may further comprise protrusions 134 extending from the inner surface of the knot body 124 toward the longitudinal axis. Protrusions 134 may be formed as rings as illustrated, or as spirals, spikes, bumps, or other suitable structures or combinations of structures.

Referring to FIGS. 5 and 10, in one embodiment, the knot body 124 may be located distally from the plug 126 within the outer tube 114. The plug is preferably sized to be inserted into the inner cavity of the knot body 124, and may have a tapered configuration as shown in FIG. 10. Alternatively, the plug 126 may have a constant cross-section over a majority of its length, such as shown in FIG. 5, with a tapered, chamfered or rounded distal end for facilitating insertion into the knot body 124. The outer dimension of the plug 126 may be slightly larger than the inner dimension of the cavity of the knot body 124, such that when the plug is inserted into the cavity, a relatively secure fit is provided between the two. The protrusions 134 within the knot body further facilitate the relative securement. The plug 126 may also comprise indentations, not shown, for receiving the protrusions 134 to secure the plug 126 more surely in the knot body 124. Other embodiments are contemplated wherein protrusions are formed on the plug 126 with or without indentations formed in the inner cavity of the knot body 124. It is also contemplated that in some embodiments both the plug 126 and the knot body 124 may comprise protrusions and indentations, respectively. In certain embodiments, insertion of the plug 126 into the knot body 124 may cause the knot body 124 to slightly expand. Both the knot and the knot body may be formed of any suitable resilient materials, and in one embodiment, are made from the same material as the suture, more preferably polypropylene.

Figure 19:
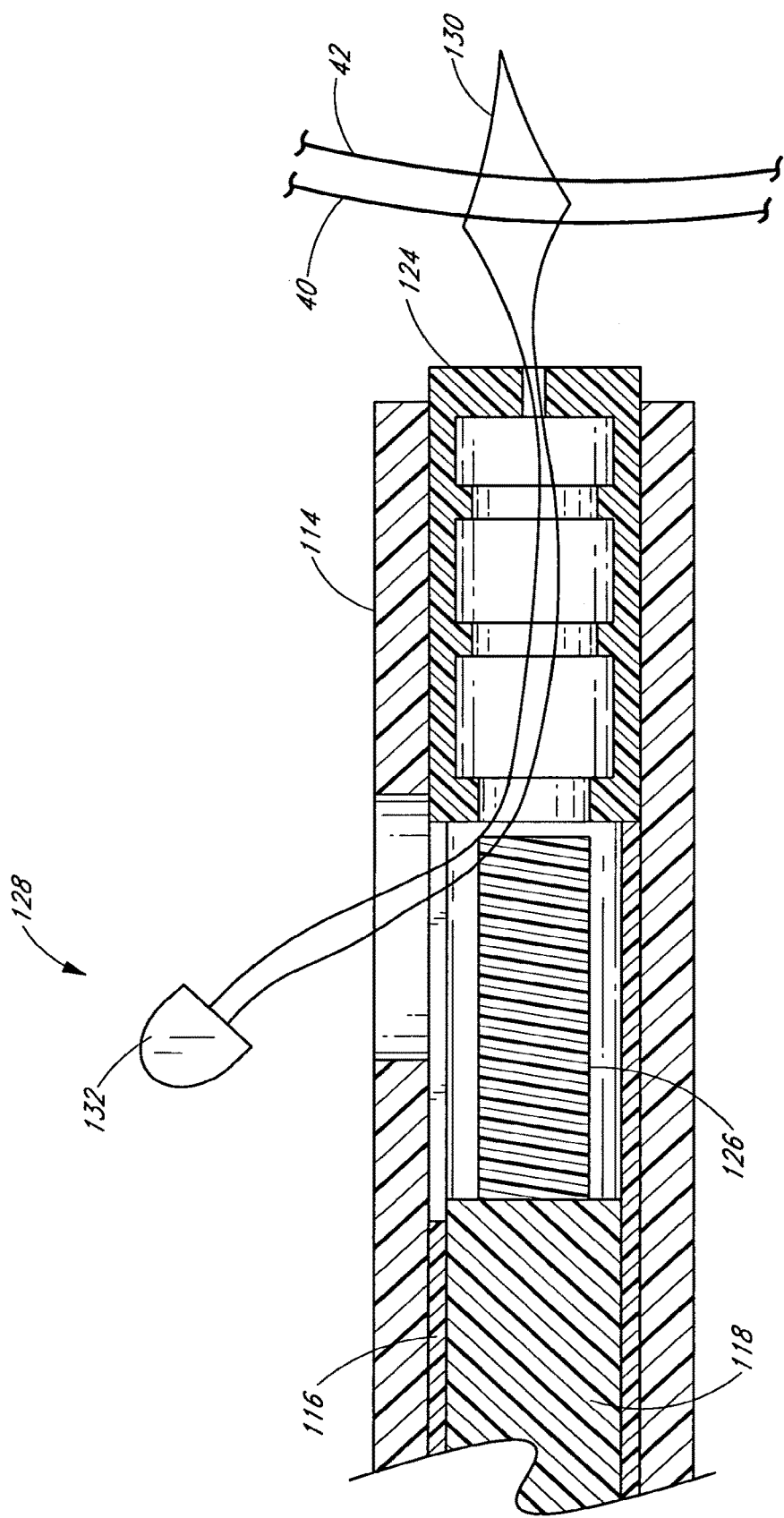
FIG. 19 is a partial cross-sectional view of a knot placement device, with suture ends passing through a threader.
Figure 20:
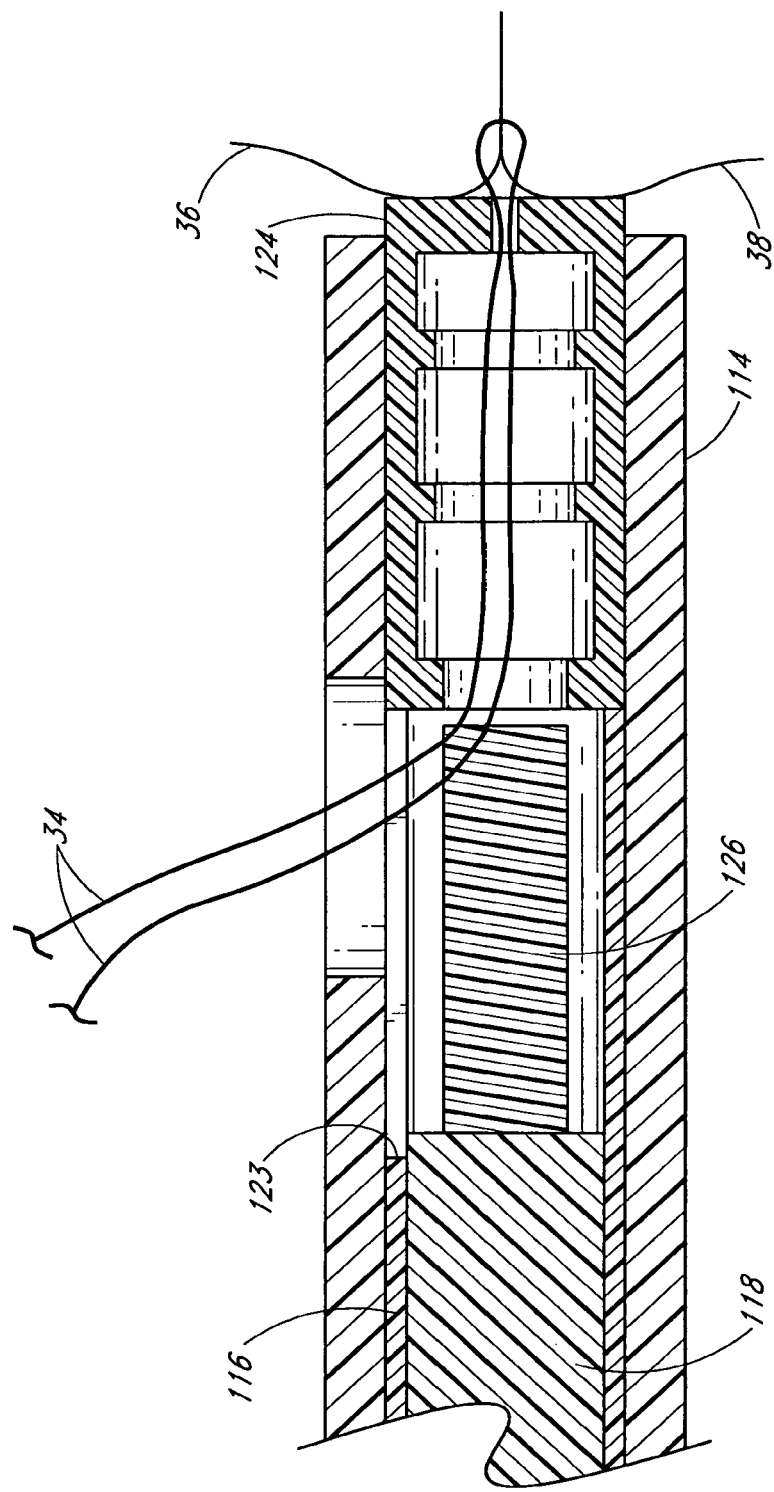
FIG. 20 illustrates the device of FIG. 19 having two suture portions passing therethrough, with the distal end of the device in contact with a tissue portion.
Figure 21:
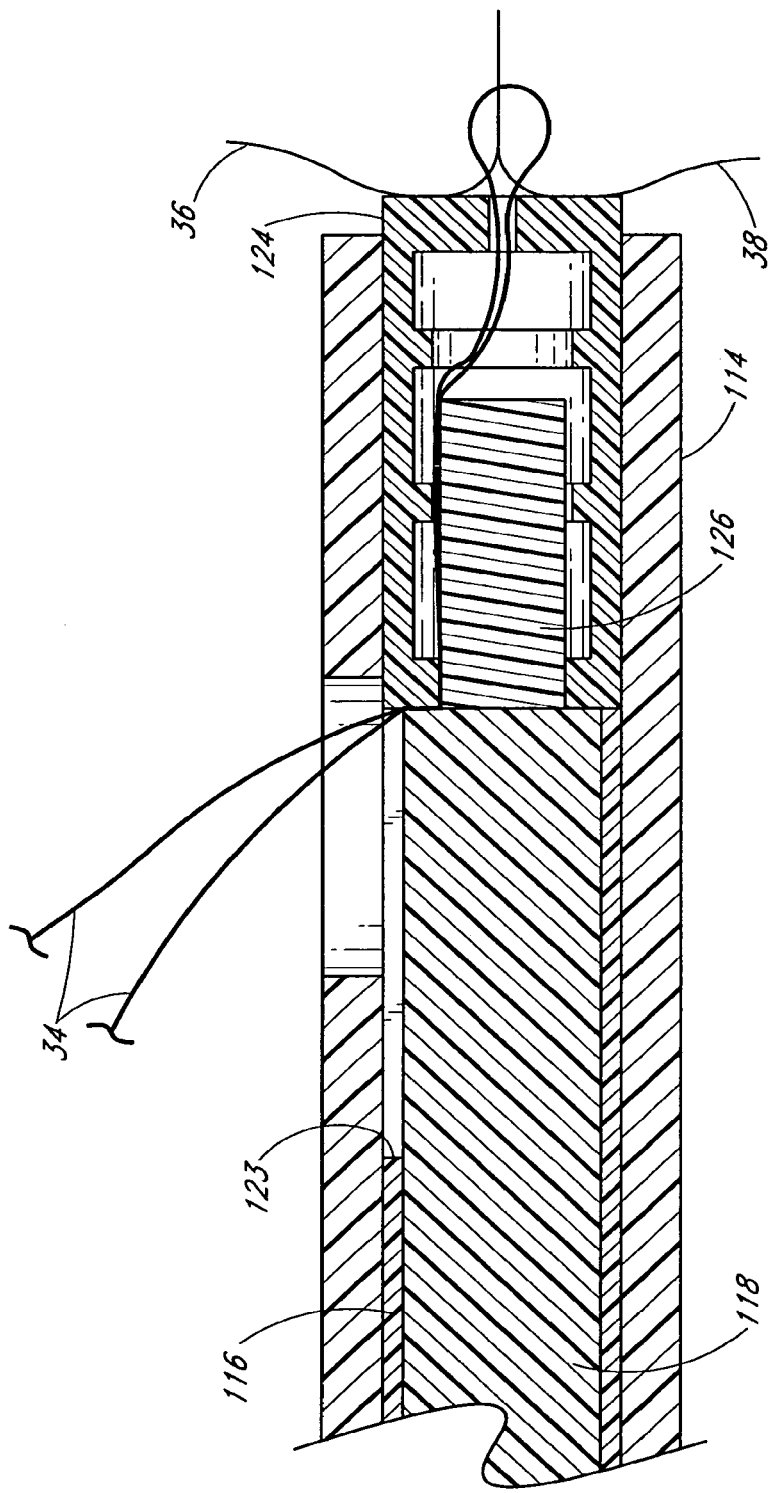
FIG. 21 illustrates the device of FIGS. 19-20 with the push rod being advanced until the plug is inserted into the knot body, trapping the suture portions between the plug and knot body.
Figure 22:
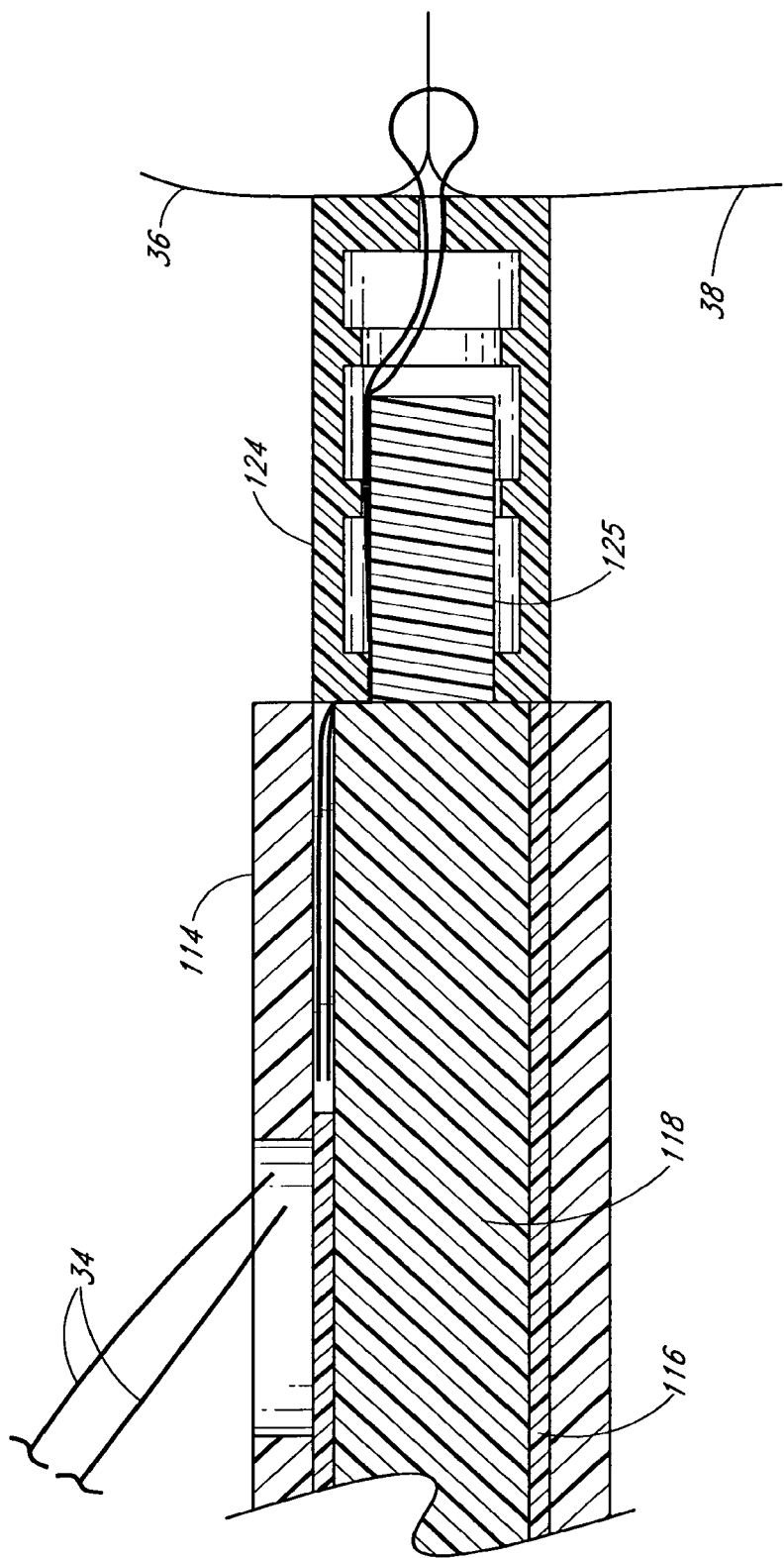
FIG. 22 illustrates the device of FIGS. 19-21, the push rod being further advanced, the intermediate tube also being advanced to eject the knot from the device and sever the suture portions.
Figure 23:
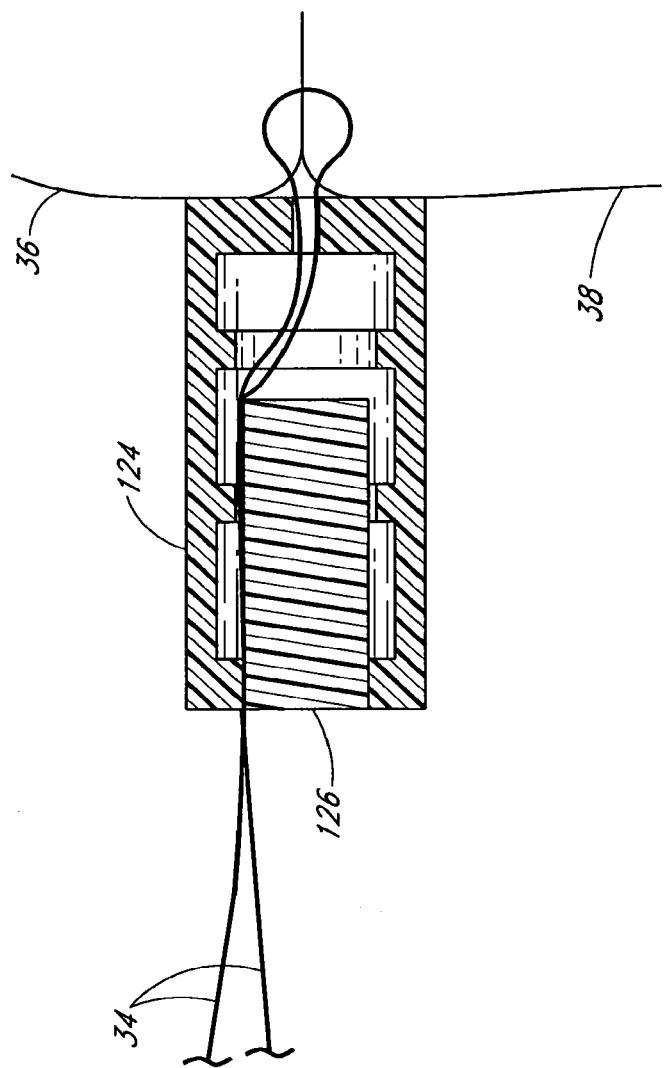
FIG. 23 illustrates the knot of FIGS. 19-22, in its final placement.

FIGS. 19-23 illustrate one embodiment for placing a knot utilizing the knot placement device 100 described above. With reference to FIG. 19, a pair of sutures ends 40 and 42 may be passed through the loop 130 of threader 128. The threader is preloaded into the knot placement device 100 as described above. The tab 132 of threader 128 may be pulled proximally to dispose suture 34 in the device, as shown in FIG. 20. Suture 34 may be held in tension, by hand or otherwise, while the device 100 is advanced until the knot body 124 or shaft 104 contacts at least one of tissue portions 36 and 38, as illustrated in FIG. 20. The actuator 106 may be depressed to advance the push rod 118, thereby forcing the plug 126 distally into the knot body 124 and trapping suture 34 there between the plug 126 and the knot body 124, as shown in FIG. 21. The actuator may be further depressed until the cam 108 contacts the proximal end of intermediate tube 116, causing the intermediate tube 116 to contact knot body 124 and eject the knot from the shaft 104. As shown in FIG. 22, advancement of intermediate tube 116 may also cause cutting surface 123 to sever suture 34 where it extends out of opening 120. The knot placement device may then be removed, leaving the knot in place against the tissue portions, as shown in FIG. 23.

In one embodiment, the knot may be ejected from the shaft 104 while leaving the sutures 34 un-severed. For example, the knot may be ejected before the cutting surface 123 reaches the suture 34. In another embodiment, no intermediate tube is provided, and the suture may be cut manually.

In an embodiment including the intermediate tube, the device 100 may be configured such that the distal ends of the outer tube 114, intermediate tube 116, and the push rod 118 lie generally flush relative to one another and are held relatively in position. This position may be held, for example, by depressing the actuator until it rests in a detent in cam 108. The detent may signal to the user that the plug 126 has been inserted into knot body 124, but also that the sutures 34 have not been cut. At such time, the placement device may be used to further advance the knot against tissue portions 36 and 38 using the distal end surface of the shaft. The actuator may be further depressed to advance the push rod 118 and intermediate tube 116 to sever sutures 34.

The actuator 106 and cam 108 may also be provided with locking mechanisms that prevent the actuator 106 from returning to its original position. Further details are provided in application Ser. No. 11/235,751 filed Sep. 27, 2005, the entirety of which is hereby incorporated by reference. Such an embodiment may be advantageous to hold the push rod flush with the distal end of the outer tube to provide a surface that can be utilized to further advance and position the knot against tissue portions 36 and 38.

It will be appreciated that other embodiments are contemplated without use of the intermediate tube, but are still capable of severing the suture. For example, the push rod may be provided with portions of differing diameter. A distal, smaller diameter may be sized to engage the plug 126 to push the plug into the knot body 124. A proximal, larger diameter may be provided on the push rod, which includes a sharpened surface at the transition between the larger and smaller diameter sections. Once the smaller portion of the push rod pushes the plug 126 into the knot body 124, the larger portion of the push rod may engage the knot body 124 to push the knot out of the placement device, while the sharpened surface on the push rod may sever the suture.

In the embodiment described above, when the knot body 124 and the plug 126 as described above are secured together, suture portions extending through the inner cavity of the knot body from opening 136 to opening 138 will be fixedly secured therein, forming a knot. It will be appreciated that many other embodiments are possible for forming a knot, including various other shapes and configurations for the knot body and plug, as well as embodiments wherein only one component may be used to provide securement relative to a suture. It will also be appreciated that in those embodiments in which the knot comprises a knot body and plug, the plug may be located within the shaft proximally from the knot body or the knot body may be located within the shaft proximally from the plug.

Figure 11:
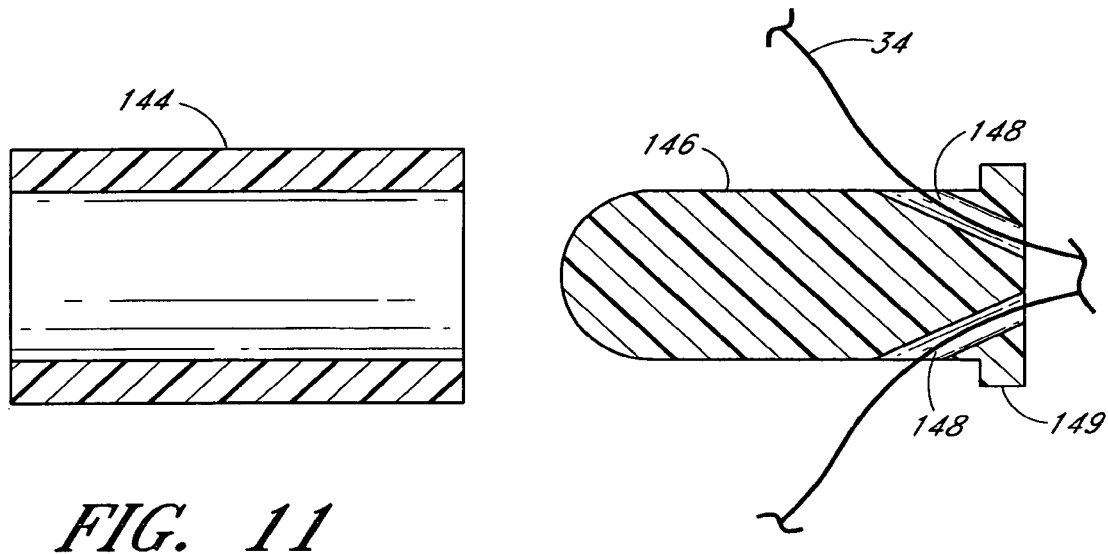
FIG. 11 is a cross-sectional side view of another embodiment of a knot.

For example, in another embodiment of a knot, shown in FIG. 11, a plug 146 is provided having a pair of holes 148 extending divergently from one end of the plug (e.g., a proximal end) to the diametrically opposed, outer surfaces of the plug. A shoulder 149 of increased outer diameter may be located at one end of plug 146 (e.g., the proximal end). When the plug 146 is inserted into a hollow knot body, the plug 146 and knot body 144 cooperate to secure the suture 34 therebetween.

Figure 12:
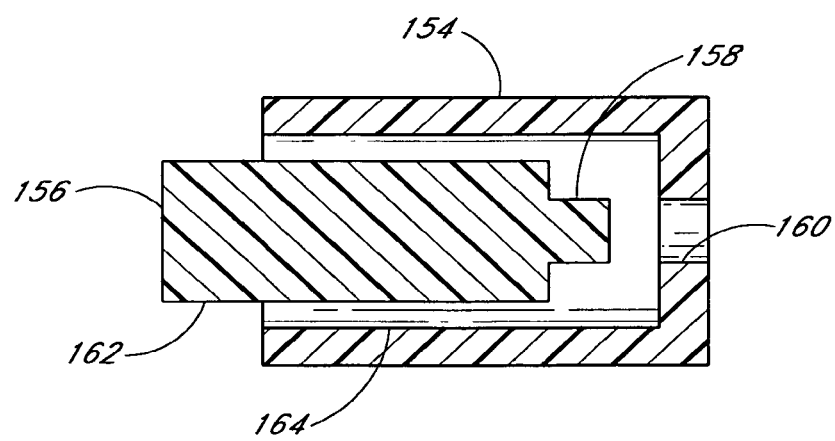
FIG. 12 is a cross-sectional side view of another embodiment of a knot.

In another embodiment, shown in FIG. 12, a plug 156 may comprise two sections having different outer diameters. A knot body 154 has an opening 136 with an inner surface 160. A surface 162 of plug 156 may have a smaller diameter than an interior surface 164 of knot body 154. A surface 158 of plug 156 may have a diameter such that surface 158 engages surface 160 of knot body 154 and cooperate to hold suture portions securely therein.

In another embodiment, shown in FIGS. 13 and 14, a plug 176 comprises a longitudinally-extending slot 178 such that plug 176 is generally fork-shaped. The slot 178 extends from the distal end partially to the proximal end. Suture 34 extends through the knot body 174, through the slot 178, and out from the plug 176, preferably on opposite sides of the plug 176. Insertion of the plug 176 into knot body 174 preferably causes compression of the slot to securely fix the suture portions within the slot. It will be appreciated that in this embodiment, the knot placement device can either be actuated to move the plug distally into the knot body, or alternatively, may be actuated to move the knot body distally over the plug.

Figure 15:
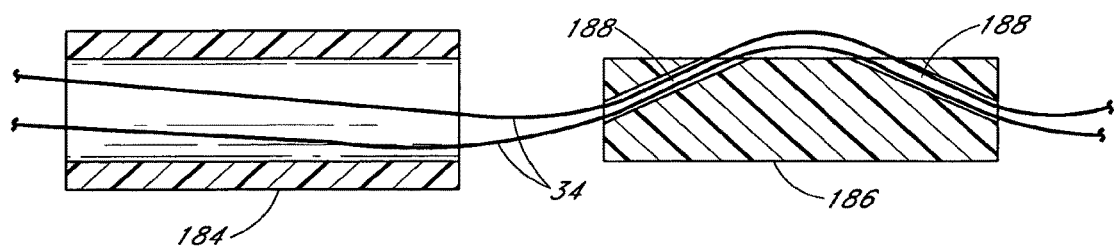
FIG. 15 is a cross-sectional side view of another embodiment of a knot.

In another embodiment, shown in FIG. 15, a pair of side holes 188 are provided at spaced locations along the length of a plug 186. Suture portions pass from an end hole at one end of the plug 186, outwardly through one of the side holes, and then inwardly back into the body of the plug and out an opposite end hole. When the knot body 184 is slid over the plug, either by being advanced distally over the plug or by having the plug advanced distally into the knot body, the suture 34 is secured relatively between the plug and the knot body.

Figure 16A:
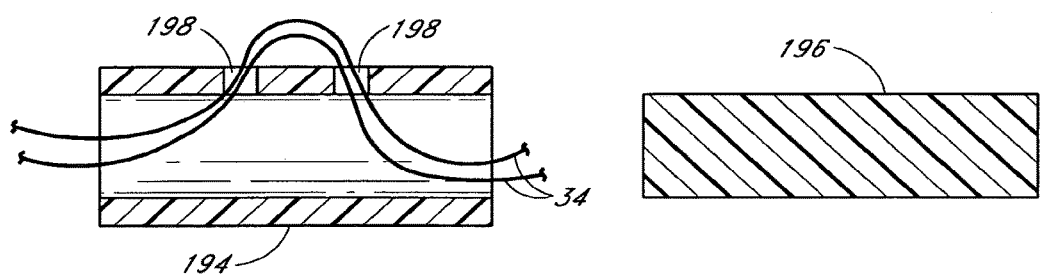
FIG. 16a is a cross-sectional side view of another embodiment of a knot and illustrating a routing of a suture through the knot body.
Figure 16B:
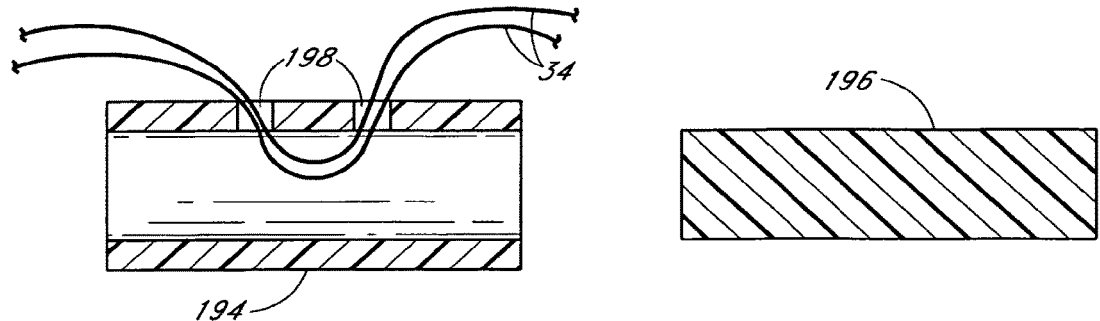
FIG. 16b is a cross-sectional side view of the embodiment of the knot of FIG. 16a and illustrating an alternative routing of a suture through the knot body.

In another embodiment, shown in FIGS. 16a and 16b, a knot body 194 comprises two side holes 198. Suture 34 may be routed through knot body 194 either from within the body, out through one of the side holes, and back into the body through the other side hole, as shown in FIG. 16a, or may be routed into one of the side holes from outside the body, into the body, and then out the other side hole, as shown in FIG. 16b. In either embodiment, a plug 196 may then be used to secure the suture relative to the knot body.

Figure 17A:
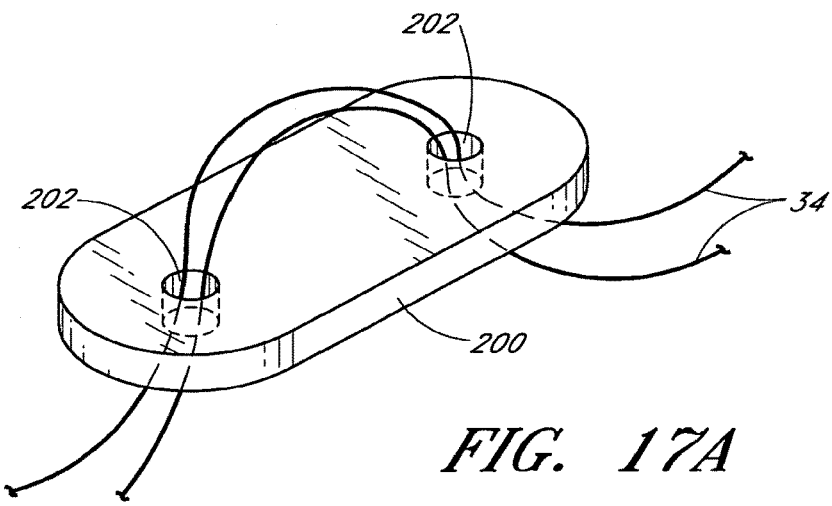
FIG. 17a is a perspective view of another embodiment of a knot.
Figure 17B:
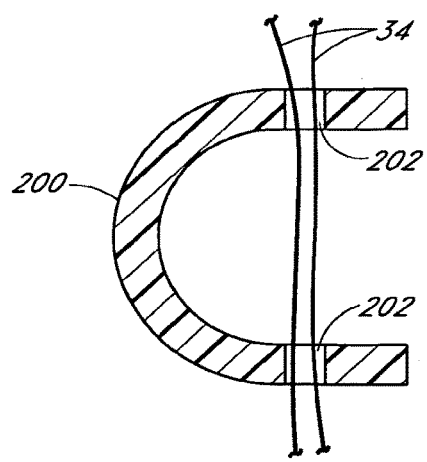
FIG. 17b is a cross-sectional side view of the embodiment of a knot shown in FIG. 17.

In another embodiment, shown in FIGS. 17a and 17b, a knot 200 comprises a single component or knot body. A plate, ring or other structure, such as a flat resilient member, may be provided with two holes 202. As shown in FIG. 17b, the plate is bent to form a "U" shape, to allow the suture 34 to be passed therethrough. The plate may be made of an elastic or shape memory material which springs back to its flattened configuration, shown in FIG. 17a, which locks the suture in place relative to the plate. Other embodiments are also contemplated in which suture portions are provided through a tortuous path of a knot body. A threader as described above may be used to guide the suture portions through the knot body while it is positioned within a knot placement device. Once ejected from the knot placement device, the knot body may assume a different configuration which locks the suture in place relative to the knot body.

Figure 18A:
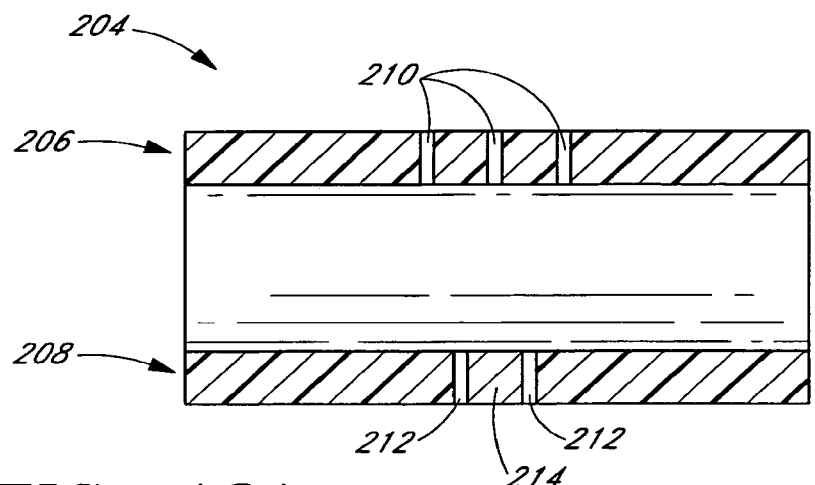
FIG. 18a is a cross-sectional side view of another embodiment of a knot.
Figure 18B:
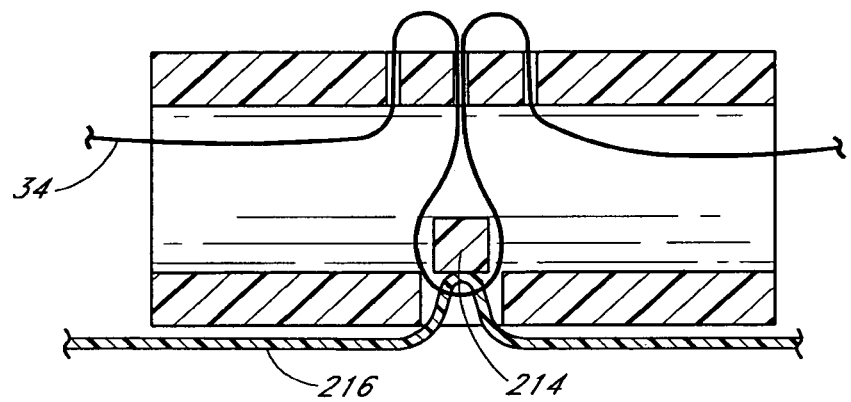
Figure 18C:
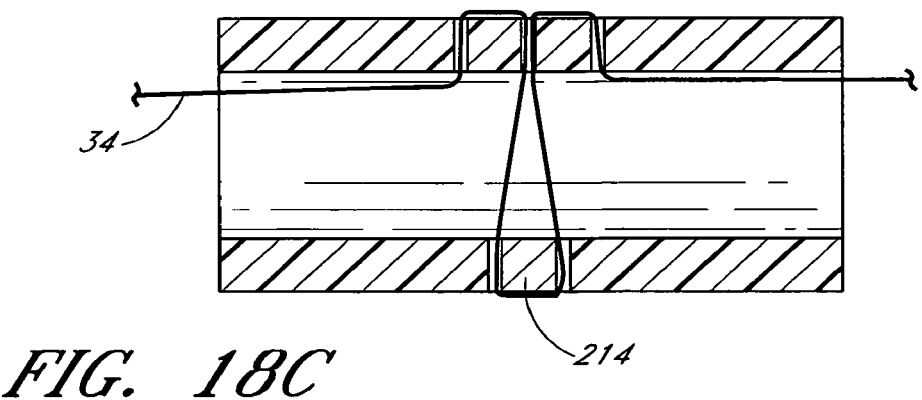
FIG. 18c is a cross-sectional side view of the knot of FIGS. 18a-18b.

In another embodiment, shown in FIGS. 18a, 18b, and 18c, a knot 204 comprises a tube having an upper wall 206 and a lower wall 208. The upper wall comprises three linearly-spaced apertures 210. The lower wall comprises two apertures 212 to create a displaceable section 214 in the lower wall 208. The displaceable section 208 is displaced toward the center of the knot 204 by any suitable means, such as a curved rod 216 as illustrated in FIG. 18b. A suture 34 is threaded in and out of the apertures 210 in the upper wall and around the displaceable section 214 of the lower wall. As the knot 204 is ejected from the knot placement device, the displaceable section 214 is allowed to move toward its original position to more surely secure the suture 34 within the knot 204 as illustrated in FIG. 18c.

Figure 24:
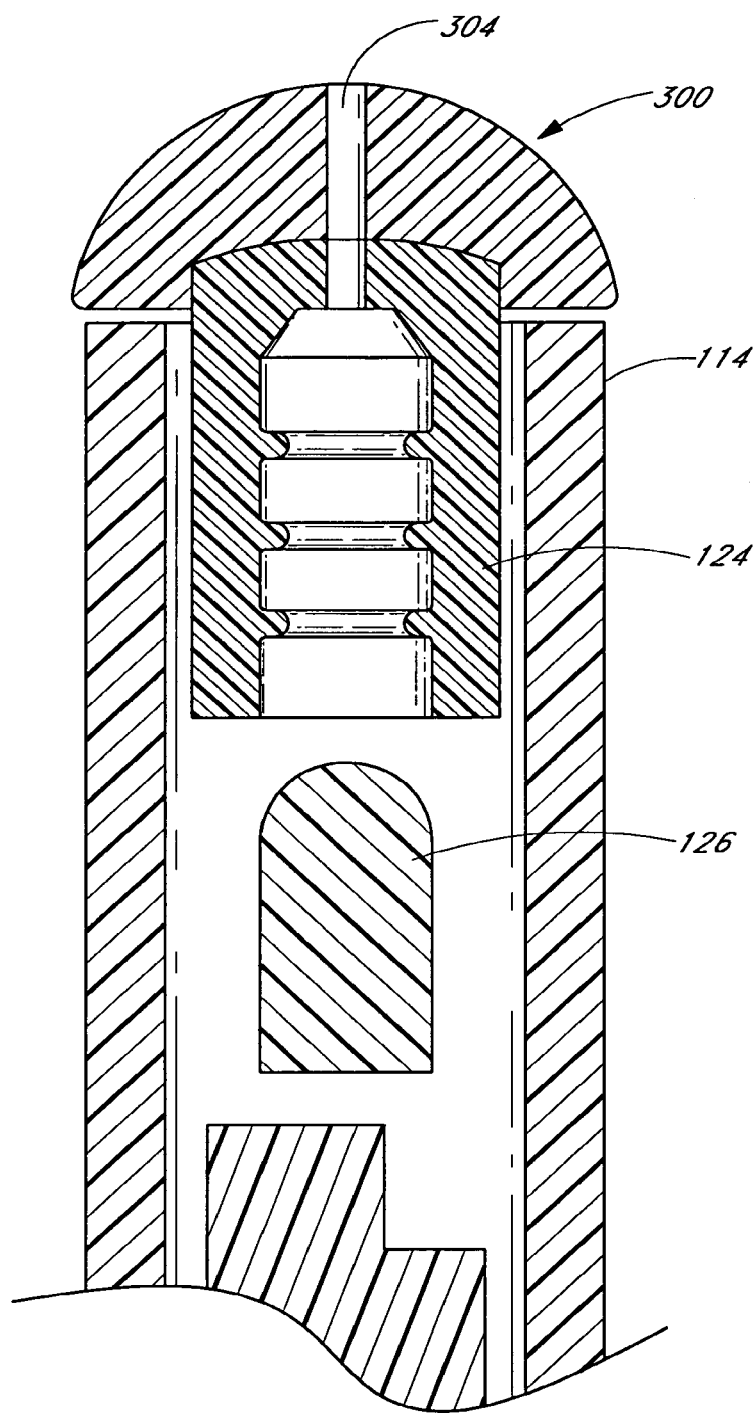
FIGS. 24 and 25 illustrate another embodiment of a knot having an atraumatic tip.
Figure 25:
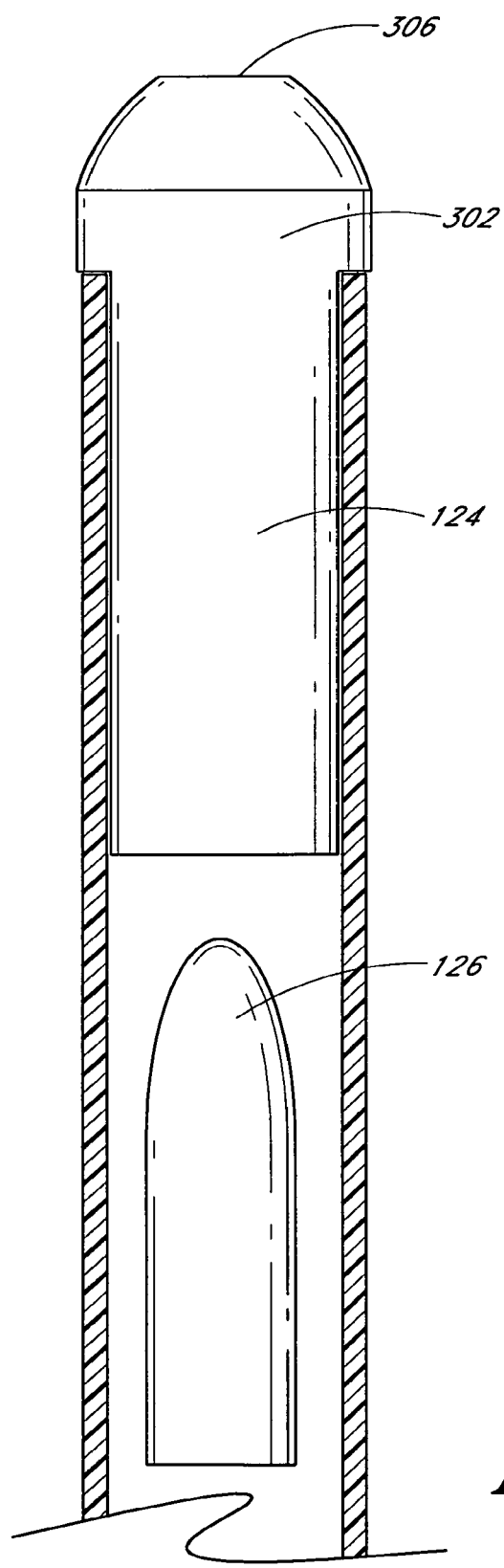

In another embodiment, shown in FIGS. 24 and 25, a knot comprises a knot body 124 and a plug 126 such as described above, but with the knot body having an atraumatic tip 300. The tip 300 may be rounded and have an outer diameter about the same as that of the outer tube 114. As shown more particularly in FIG. 25, the tip may have a flat transition 302 as well. The tip 300 may be integrally formed with the knot body 124 or may be separately attached. As illustrated, the tip 300 may have an aperture 304 extending axially through the tip, opening to the cavity inside the knot body. When the knot is delivered into a patient as described above, the atraumatic tip prevents damage to the patient.

Various other embodiments are contemplated for the knot. For example, a knot may simply comprise a tube with a sufficiently small inner diameter through which suture portions may be positioned and held. In another embodiment not shown, the plug may comprise a shoulder located near its proximal end having an increased outer diameter. The shoulder may not be inserted into the knot body, but may be used to push the knot out of the placement device once the plug has been inserted into the knot body.

It should be understood that certain variations and modifications of this invention will suggest themselves to one of ordinary skill in the art. The scope of the present invention is not to be limited by the illustrations or the foregoing descriptions thereof.

What is claimed is:

1. A knot placement device comprising:
a handle having proximal and distal ends, the proximal end of the handle defining a proximal most end of the knot placement device;
an elongate shaft with proximal and distal ends and a lumen extending therethrough, the proximal end of said shaft directly coupled to said handle, the distal end of the handle located closer to the proximal end of said shaft than to the distal end of said shaft throughout use of the knot placement device, the elongate shaft further comprising a single continuous wall from the proximal end to the distal end with a side hole near its distal end and spaced proximal from the distal end;
a push rod having proximal and distal ends slidably disposed in the lumen of said elongate shaft, the proximal end of said push rod extending into said handle;
an actuator located on said handle, wherein activating said actuator distally advances said push rod relative to said elongate shaft; and
a knot comprising a knot body and a plug, said knot positioned in the lumen of the elongate shaft at the distal end thereof, at least a portion of the knot body surrounded circumferentially and continuously by a portion of the elongate shaft distal of the side hole;
wherein at least one of the knot body and the plug is configured to receive at least one suture portion extending into the lumen of the elongate shaft at the distal end with the at least one suture portion exiting the shaft through the side hole;
wherein distal advancement of the push rod moves the plug relatively into the knot body to secure the at least one suture portion, and further distal advancement of the push rod causes the knot to eject from the lumen of the shaft.

2. The knot placement device of claim 1, wherein the plug is positioned proximally of the knot body within the lumen of the shaft, such that distal advancement of the push rod pushes the plug into the knot body.

3. The knot placement device of claim 1, wherein continuous distal advancement of the push rod moves the plug relatively into the knot body and ejects the knot from the lumen of the shaft.

4. The knot placement device of claim 1, wherein the actuator comprises a locking mechanism configured to lock the position of the push rod.

5. The knot placement device of claim 4, wherein the locking mechanism is configured to lock the push rod once the push rod has been distally advanced.

6. The knot placement device of claim 1, further comprising a cutting edge movable within the elongate shaft, the cutting edge configured to cut the at least one suture portion after distal advancement of the push rod moves the plug relatively into the knot body to secure the at least one suture portion.

7. A knot placement device comprising:
- a handle having proximal and distal ends, the proximal end of the handle defining a proximalmost end of the knot placement device;
- an elongate shaft with proximal and distal ends and a lumen extending therethrough, the proximal end of said shaft directly coupled to said handle, wherein a greater portion of the elongate shaft is located external to the handle than a portion of the elongate shaft located internal to the handle throughout use of the knot placement device, the elongate shaft further comprising an opening near its distal end;
- a push rod having proximal and distal ends movably disposed in the lumen of said elongate shaft, the distal end of said push rod configured to move a knot plug into a knot plug body to form a knot by securing at least one suture portion between the knot plug and the knot plug body with the at least one suture portion passing through the opening in the elongate shaft;
- a cutting edge movable within the elongate shaft, the cutting edge configured to cut the at least one suture portion after forming the knot; and
- an actuator located on said handle, said actuator connected to the proximal end of the push rod and configured to activate distal advancement of said push rod relative to said elongate shaft.

8. The knot placement device of claim 7, wherein the cutting edge moves longitudinally to cut the at least one suture portion.

9. The knot placement device of claim 7, wherein the opening is a hole spaced proximally from the distal end of the elongate shaft.

10. The knot placement device of claim 7, wherein the actuator comprises a locking mechanism configured to lock the position of the push rod.

11. The knot placement device of claim 10, wherein the locking mechanism is configured to lock the push rod once the push rod has been distally advanced.

* * * * *

UNITED STATES PATENT AND TRADEMARK OFFICE
CERTIFICATE OF CORRECTION

PATENT NO. : 9,642,616 B2
APPLICATION NO. : 13/905225
DATED : May 9, 2017
INVENTOR(S) : Anthony A. Nobles It is certified that error appears in the above-identified patent and that said Letters Patent is hereby corrected as shown below:

On the Title Page

In Column 2 (page 5, item (56)) at Line 70, under Other Publications, change "byJohn" to --by John--.

In Column 2 (page 5, item (56)) at Line 70, under Other Publications, change "&Sons," to --& Sons,--.

In Column 2 (page 5, item (56)) at Line 72, under Other Publications, change "ai," to --al,--.

In Column 1 (page 6, item (56)) at Line 14, under Other Publications, change "B.SaundersCo.," to --B. Saunders Co.,--.

In Column 1 (page 6, item (56)) at Line 22, under Other Publications, change "copyright1977" to --copyright 1977--.

In the Specification

In Column 1 at approximately Line 11, change "Jun," to --Jun.--.

In Column 1 at approximately Line 12, change "60/009,485," to --60/709,485,--.

In the Claims

In Column 11 at approximately Line 6, in Claim 7, change "proximalmost" to --proximal most--.

Signed and Sealed this
Fifth Day of December, 2017

Joseph Matal
*Performing the Functions and Duties of the
Under Secretary of Commerce for Intellectual Property and
Director of the United States Patent and Trademark Office*